(12) United States Patent
Allum et al.

(10) Patent No.: US 9,199,053 B1
(45) Date of Patent: Dec. 1, 2015

(54) METHODS, SYSTEMS AND DEVICES FOR VENTILATION USING A NASAL VENTILATION MASK WITH A MANIFOLD AND INTERNAL COMPLIANT TUBE AND NASAL SEALING CUSHION ASSEMBLY

(75) Inventors: Todd W. Allum, Livermore, CA (US); Darius Eghbal, Oakland, CA (US); Jose J. Aguirre, Jr., Laguna Niguel, CA (US); Anthony D. Wondka, Thousand Oaks, CA (US); Joseph Cipollone, Laguna Niguel, CA (US)

(73) Assignee: Breathe Technologies, Inc., Irvine, CA (US)

( * ) Notice: Subject to any disclaimer, the term of this patent is extended or adjusted under 35 U.S.C. 154(b) by 781 days.

(21) Appl. No.: 13/363,149

(22) Filed: Jan. 31, 2012

Related U.S. Application Data

(60) Provisional application No. 61/438,112, filed on Jan. 31, 2011.

(51) Int. Cl.
  *A61M 16/06* (2006.01)
  *A61M 16/00* (2006.01)

(52) U.S. Cl.
  CPC ........... *A61M 16/0666* (2013.01); *A61M 16/00* (2013.01); *A61M 16/06* (2013.01)

(58) Field of Classification Search
  CPC ..... A61M 15/00; A61M 15/08; A61M 16/00; A61M 16/0461; A61M 16/06; A61M 16/0666; A61M 16/0672; A61M 16/085; A61M 16/0858; A61M 16/0677; A61M 16/208; A61M 16/209; A61M 16/1095; A61M 16/109; A61M 16/0683; A61M 16/08; A61M 16/16; A61M 16/0057; A61M 16/0866; A61M 16/0627; A61M 16/161; A61M 16/0069; A61M 16/122; A61M 16/0833; A61M 5/142; A61M 5/172; A61M 15/0028; A61M 15/0033; A61M 16/0493; A61M 16/127; A61M 16/1075; A61M 16/0009; A61M 16/125; A61M 16/0051; A61M 16/0694; A61M 16/0633; A61M 16/0605; G01N 33/497; G01N 1/22; G01N 33/004; G01N 21/3504; G01N 21/05; A61B 5/097; A61B 5/6819; A61B 5/087; A61B 5/085; A61B 5/682; A61B 5/0873; A61B 5/411; A61B 5/083; A61B 5/4806; A61B 5/0836; A61B 5/01; A61B 5/038; A61B 5/4818; A61B 5/0878; G06Q 50/22; G06Q 50/24; A62B 18/025; A62B 9/003; A62B 7/00; A62B 18/02; A62B 18/08
  USPC ............. 128/200.24, 200.26, 203.22, 204.18, 128/204.21, 204.23, 205.25, 206.21, 128/206.28, 207.13, 207.18
  See application file for complete search history.

(56) References Cited

U.S. PATENT DOCUMENTS 3,714,944 A * 2/1973 Price et al. ............... 128/203.12
3,894,537 A * 7/1975 Camp ....................... 128/203.17

(Continued)

FOREIGN PATENT DOCUMENTS

WO  WO2010115170  10/2010

OTHER PUBLICATIONS

European Search Report and Written Opinion for EP12742707.8. Issued Feb. 12, 2015.

*Primary Examiner* — Annette Dixon
(74) *Attorney, Agent, or Firm* — Stetine Brunda Garred & Brucker

(57) ABSTRACT

Embodiments of the present invention may provide ventilation to a patient's lung or airway using a nasal ventilation mask, as part of either a non-invasive ventilation system (NIV) or a non-invasive open-airway ventilation system (NIOV). A ventilation mask may include a rigid or semi-rigid manifold housing. A compliant tube may be located within the manifold housing for forming a main gas pathway through the manifold housing. One or more nasal connectors may be fluidly coupled to the main gas pathway in the compliant tube. A system for sensing airflow through a patient's nose may include a sensing port with a distal opening that opens to a main gas pathway. A protrusion on at least one side of the distal opening may protrude into the main gas pathway.

37 Claims, 14 Drawing Sheets

(56) References Cited

U.S. PATENT DOCUMENTS

| | | | |
|---|---|---|---|
| 3,906,996 A * | 9/1975 | DePass et al. | 137/893 |
| 4,602,644 A * | 7/1986 | DiBenedetto et al. | 600/538 |
| 4,989,599 A * | 2/1991 | Carter | 128/207.18 |
| 5,474,060 A * | 12/1995 | Evans | 128/204.22 |
| 8,220,463 B2 * | 7/2012 | White et al. | 128/207.18 |
| 8,701,667 B1 * | 4/2014 | Ho et al. | 128/206.24 |
| 8,701,668 B2 * | 4/2014 | Selvarajan et al. | 128/207.18 |
| 2004/0015092 A1 * | 1/2004 | Pettersson | 600/532 |
| 2009/0165799 A1 * | 7/2009 | Duquette et al. | 128/204.25 |

* cited by examiner

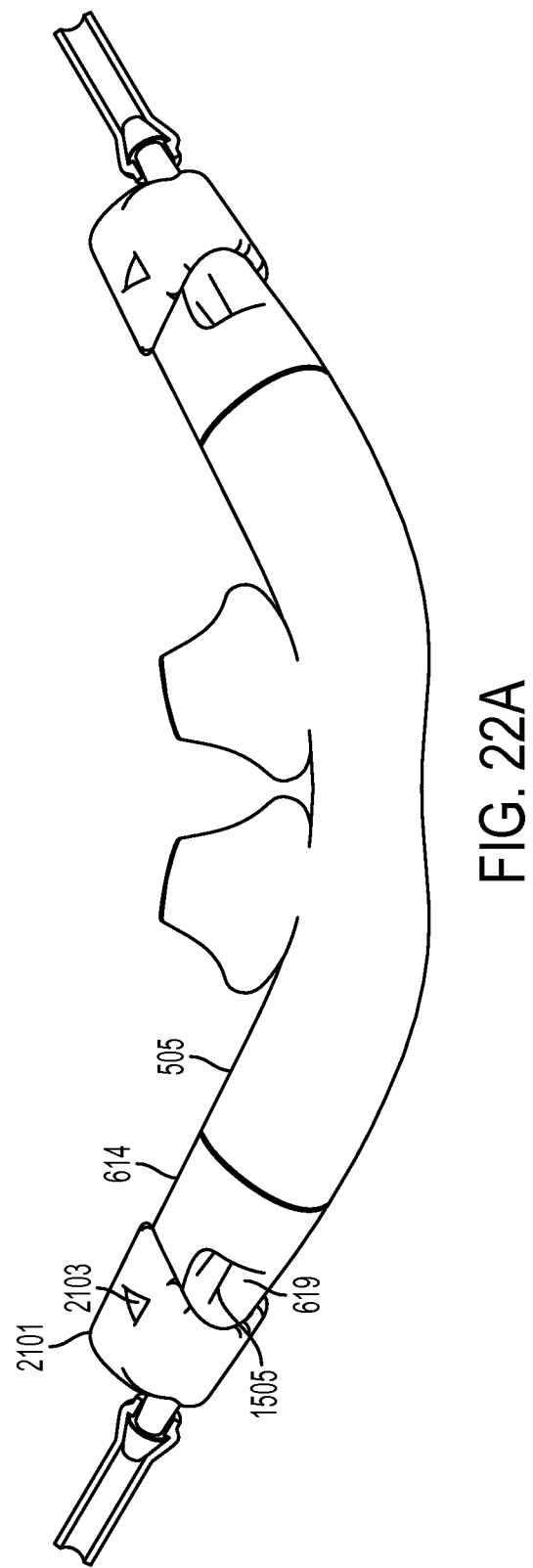

▓ AIR INHALED SPONTANEOUSLY BY PATIENT
▨ GAS DELIVERED BY THE VENTILATOR TO THE LUNG
▦ GAS DELIVERED BY THE VENTILATOR BUT NOT REACHING THE LUNG AND WASTED TO AMBIENT
▧ AIR ENTRAINED BY THE VENTILATOR AND MASK INTO THE PATIENT'S LUNG

METHODS, SYSTEMS AND DEVICES FOR VENTILATION USING A NASAL VENTILATION MASK WITH A MANIFOLD AND INTERNAL COMPLIANT TUBE AND NASAL SEALING CUSHION ASSEMBLY

CROSS-REFERENCE TO RELATED APPLICATIONS

This application claims priority to U.S. Provisional Patent Application No. 61/438,112, filed Jan. 31, 2011; the content of which is incorporated by reference herein in its entirety.

FIELD OF THE INVENTION

The present invention relates to the field of ventilation therapy for persons suffering from respiratory and breathing disorders, such as respiratory insufficiency and sleep apnea. More specifically, the present invention relates to providing ventilation using nasal ventilation masks that are unobtrusive and unencumbering.

BACKGROUND OF INVENTION

There is a need for a minimally obtrusive nasal mask and ventilation system that delivers mechanical ventilatory support or positive airway pressure, and which unencumbers the patient. There is a range of clinical syndromes that require ventilation therapy that would benefit from such a mask and system, such as respiratory insufficiency, airway or sleeping disorders, congestive heart failure, neuromuscular disease, and a range of situations that would be benefited, such as chronic, acute, emergency, mass casualty and pandemic situations.

Oxygen therapy is available with devices that do not encumber the patient; however, oxygen therapy is used for far less severe forms of clinical syndromes compared to ventilation therapy. For example, some nasal mask oxygen therapy systems have been developed for the purpose of delivering mixtures of air and oxygen by entraining air into the mask. These are not considered ventilation therapy or respiratory support, however, because they do not mechanically help in the work of breathing. Recently, a variant of oxygen therapy has been employed, known as high flow oxygen therapy (HFOT). In this case, the oxygen flow rate is increased beyond standard long term oxygen therapy (LTOT), for example, above 15 LPM. Because of the high flow rate, the oxygen must be humidified to prevent drying out the patient's airway. It has been reported that HFOT can slightly reduce the patient's absolute pleural pressure during spontaneous breathing, thus have a slight effect on work of breathing. These systems are inefficient in that they consume a significant quantity of oxygen, rendering them non-mobile systems and encumbering the patient.

Respiratory support and ventilation therapies exist that provide mechanical ventilation (MV) to the patient, and mechanically contribute to the work of breathing. MV therapies connect to the patient by intubating the patient with a cuffed or uncuffed tracheal tube, or a sealing face or nasal mask or sealing nasal cannula. While helpful in supporting the work of breathing, the patient interfaces used for MV are obtrusive and/or invasive to the user. These interfaces for MV do not facilitate mobility or activities of daily living, encumber a patient and are considered a drawback by many potential users. Non-invasive ventilation (NIV) exists which ventilates a patient with a face or nasal mask rather than requiring intubation, which can be an advantage in many situations. However, the patient cannot use their upper airway because the interface makes an external seal against the nose and/or mouth. Additionally, the system is not mobile. This combination of factors does not enable activities of daily living.

For treating obstructive sleep apnea (OSA), the gold standard ventilation therapy is continuous positive airway pressure (CPAP) or bilevel positive airway pressure (BiPAP), which is a variant to NIV in that the patient partially exhales through exhaust ports in the mask and back into large gas delivery tubing, rather than through an exhalation circuit as in MV. Continuous positive pressure applied by the ventilator to the patient by a nasal or face mask that seals against the nose or face prevents upper airway obstruction. While effective, this therapy has poor patient compliance because the patient interface is obtrusive to the patient and the patient unnaturally breathes through both a mask and gas delivery circuit.

In summary, existing therapies have several disadvantages. These disadvantages include, but are not limited to, not offering respiratory support or airway support in a manner that unencumbers the patient. Additionally, existing therapies: (1) are invasive and/or obtrusive such that they do not allow for mobility and activities of daily living; (2) do not allow the sensation of breathing from the ambient surroundings normally; and (3) are not provided in an easily portable system or a system that can be easily borne or worn by the patient.

SUMMARY OF INVENTION

Embodiments of the present invention may provide ventilation to a patient using a nasal ventilation mask, in conjunction with either non-invasive ventilation (NIV) or non-invasive open-airway ventilation (NIOV). The ventilation mask may include (1) a manifold that is positioned under the nose that comprises a compound arcuate shape to match facial anatomy, and that structurally maintains the gas flow path geometry, and (2) a compliant nasal cushion that extends from inside the manifold and impinges with the nostrils.

Embodiments of the present invention may provide a system for providing ventilation to an individual, the system including: a rigid or semi-rigid manifold housing; a compliant tube within the manifold housing for forming a main gas pathway through the manifold housing; and one or more nasal connectors fluidly coupled to the main gas pathway in the compliant tube.

In certain embodiments of the system, a manifold housing may be a multi-piece manifold housing. The main gas pathway of the compliant tube may be devoid of corners and abrupt bends and angles. The compliant tube may be substantially straight in a relaxed state. The manifold housing may have compound arcuate curves. The compound arcuate curves may curve laterally from a midline, posteriorly and superiorly. The compliant tube may also include one or more bumps to create space between the compliant tube and an inner surface of the manifold housing. The one or more nasal connectors may each have an offset distal end relative to a base of each of the one or more nasal connectors. The one or more nasal connectors may be coupled to the manifold housing. The one or more nasal connectors may be coupled to the compliant tube within the manifold housing. A gimbaling zone of each of the one or more nasal connectors may extend below an outer surface of the manifold housing. The compliant tube and the one or more nasal connectors may be continuous. The one or more nasal connectors may be one or more nasal pillows. An inner tube retaining ring may be included for coupling the compliant tube to the manifold housing at opposite proximal ends of the compliant tube. The main gas pathway may be divided into a left gas pathway and a right gas pathway, and further may include an interconnecting channel between the left gas pathway and the right gas pathway. One or more sensing ports may be included, wherein the one or more sensing ports are located on a stem of at least one of the one or more nasal connectors, and/or a sensing tube guideway may be included within the manifold for receiving a sensing extension tube coupled to a gas delivery circuit. One or more sensing ports may be one or more sensing ports for each nostril. One or more nozzles may be located within the manifold housing for delivering ventilation gas to the individual. The manifold housing may include at least one entrainment port on one or more proximal ends of the manifold housing. The one or more entrainment ports may be one or more entrainment port on each of the one or more proximal ends of the manifold housing. The manifold housing may also include an attachment near the one or more entrainment ports for harvesting patient expired gases. The manifold housing may also include an attachment near the one or more entrainment ports for introducing additional gas, which may be oxygen.

Embodiments of the present invention may include a method of providing ventilation to an individual, the method including: providing ventilation gas to the individual, wherein the ventilation gas passes through a main gas pathway of a compliant tube within a rigid or semi-rigid manifold to one or more nasal connectors in fluid communication with the main gas pathway of the compliant tube.

In certain embodiments of the method, the main gas pathway of the compliant tube may be devoid of corners and abrupt bends and angles. The compliant tube may be substantially straight in a relaxed state. The one or more nasal connectors may be coupled to the compliant tube within the manifold housing. The main gas pathway may be divided into a left gas pathway and a right gas pathway, and may also include an interconnecting channel between the left gas pathway and the right gas pathway. One or more sensing ports may be located on a stem of at least one of the one or more nasal connectors. The manifold housing may include at least one entrainment port on one or more proximal ends of the manifold housing.

Embodiments of the present invention may include a system for sensing airflow through a patient's nose, the system including: a sensing port with a distal opening that opens to a main gas pathway; and a protrusion on at least one side of the distal opening that protrudes into the main gas pathway.

In certain embodiments of the system, the distal opening may be located proximal to the nose. The distal opening may be located near a stem of a nasal connector or a base of a nasal connector. The distal opening may be in a compliant tube. The compliant tube may be within a rigid or semi-rigid manifold. The protrusion may be located on a proximal side of the sensing port. The protrusion may extend approximately 0.01 to approximately 0.2 inches into the main gas pathway. The sensing port may be located within a manifold. The manifold may be a nasal interface or a CPAP mask.

Embodiments of the present invention may include a method of sensing airflow through a patient's nose, the method including: determining airflow passing a sensing port with a distal opening that opens to a main gas pathway; and wherein at least one side of the distal opening comprises a protrusion that protrudes into the main gas pathway.

In certain embodiments of the method, the distal opening may be located proximal to nose. The distal opening may be located near a stem of a nasal connector or a base of a nasal connector. The distal opening may be in a compliant tube. The compliant tube may be within a rigid or semi-rigid manifold. The protrusion may be located on a proximal side of the sensing port, wherein pressure created at the sensing port increases for patient expiratory flow and decreases for patient inspiratory flow. The protrusion may be located on a distal side of the sensing port, wherein pressure created at the sensing port decreases for patient expiratory flow and increases for patient inspiratory flow. The protrusion may extend approximately 0.01 to approximately 0.2 inches into the main gas pathway. The sensing port may be located within a manifold. The manifold may be a nasal interface or a CPAP mask.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention and are incorporated in and constitute a part of this specification, illustrate preferred embodiments of the invention and together with the detailed description serve to explain the principles of the invention. While these drawings only show a particular embodiment, for that embodiment they are roughly drawn to scale.

FIGS. 22A-22D show an alternate exemplary embodiment of a nasal mask with attachments at entrainment ports.

DETAILED DESCRIPTION OF THE EMBODIMENTS

Figure 1:
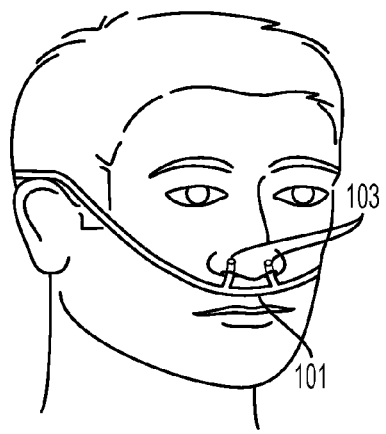
FIG. 1 shows a prior art conventional oxygen delivery cannula for administering oxygen therapy.

FIG. 1 shows a prior art conventional oxygen delivery cannula 101 for administering oxygen therapy. Extensions 103 on the cannula 101 are configured to enter nares. A proximal end (not shown) of the cannula is connected to an oxygen delivery device that delivers continuous flow oxygen at 1-6 LPM to the user's nose, or delivers a bolus of oxygen upon detection of an inspiratory effort. The system of FIG. 1 does not mechanically support the work of breathing of the patient, and is not believed to be effective in preventing moderate to severe forms of OSA. The cannula of FIG. 1 is also used with another oxygen delivery therapy, high flow oxygen therapy (HFOT), in which more than 15 LPM of humidified oxygen is delivered at a continuous flow rate to the user's nose. Due to the high flow required for HFOT, the system is non-portable and the oxygen must be humidified.

Figure 2:
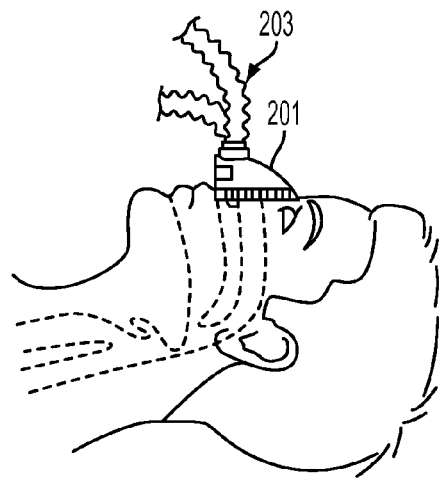
FIG. 2 shows a prior art conventional non-invasive ventilation using a nose mask and using a CPAP or BiPAP ventilation mode.

FIG. 2 shows a prior art respiratory support therapy for non-invasive ventilation (NIV), using a nasal mask 201 that is used to delivery continuous positive airway pressure (CPAP) or bilevel continuous positive airway pressure (BiPAP). NIV is used to breathe for the patient. Alternatively, NIV can be used to help the breathing of a patient, in which case the patient's spontaneous breathing effort triggers the ventilator to deliver the pressure or volume-based mechanical ventilation (MV). All of the volume delivered to and from the lungs is delivered and removed through a ventilation circuit 203 and the nasal mask 201. NIV, CPAP and BiPAP are used for respiratory insufficiency or for sleep apnea applications. NIV, CPAP and BiPAP are believed to be clinically effective, with the exception that they often become ineffective due to the encumbering and obtrusive nature of the ventilation mask and gas delivery tubing. Furthermore, NIV does not facilitate activities of daily living (ADLs) for patients with respiratory insufficiency because the ventilator cannot be borne by the patient, the patient cannot breathe room air naturally and freely because of the sealing mask, the patient's upper airway cannot function normally and naturally because it is sealed off with the external mask seal, and the gas delivery tubing is too bulky to realistically support mobility and ADLs.

The present invention may be used to provide respiratory support or airway support in a manner that is unobtrusive and/or unencumbering to the patient. When the invention is used in conjunction with NIV, the systems and methods may allow for increased patient tolerance, acceptance and adherence to the therapy. When the invention is used in conjunction with NIOV, the systems and methods not only allow for increased tolerance, acceptance and adherence, the systems and methods also facilitate mobility and activities of daily life, facilitate the sensation of breathing from ambient surroundings normally, provide an easily portable system that can be readily borne or worn by the patient, and provide gas delivery tubing that does not encumber the patient.

Figure 3:
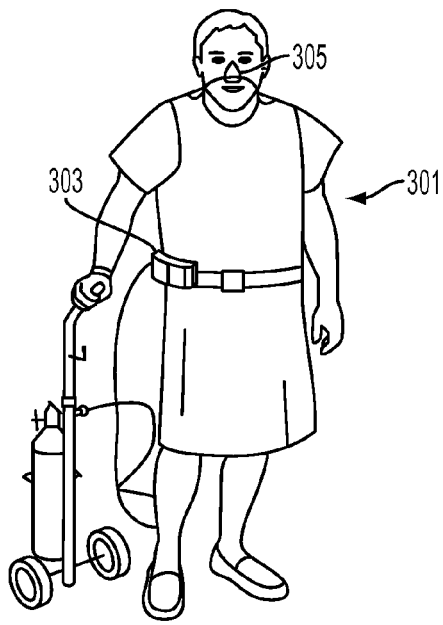
FIG. 3 shows an unencumbered patient using an embodiment of the invention to receive work of breathing support while ambulating in conjunction with an NIOV ventilation system.

FIG. 3 shows a patient 301 using a system 303 for respiratory support while ambulating, in conjunction with NIOV. With NIOV, a nasal ventilation mask 305 may be non-sealing with the nose and may allow the patient to feel like he or she is breathing naturally, but while receiving mechanical ventilatory support. The mask 305 may incorporate a special jet Venturi configuration that optimizes the performance in a small-as-possible footprint, therapy making it realistic for a patient to use the mask 305 electively and, for example, in public.

Figure 4:
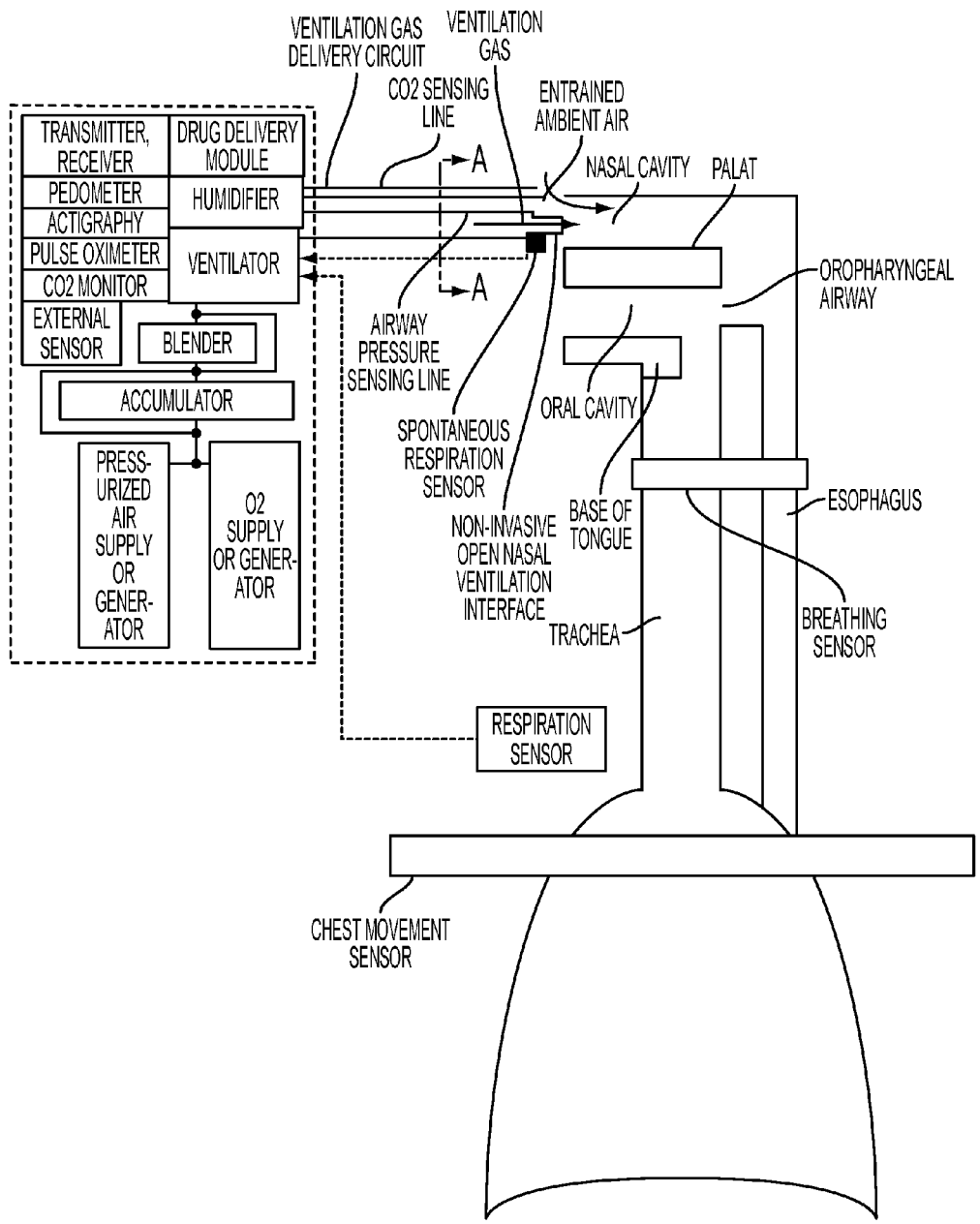
FIG. 4 is a schematic showing an exemplary system of the invention.

FIG. 4 is a block diagram schematically describing an exemplary system of the invention, including the following components: a gas source, a gas delivery system or ventilator, a gas delivery circuit and the nasal ventilation mask or interface. Additional accessory components may be included.

Gas source: A compressed oxygen source and/or a compressed air source can be included, internal or external to the ventilator module. In addition, the gas source can include oxygen and/or air generating systems, such as a compressor pump or blower to create pressurized air, an oxygen generator and/or pump to create pressurized oxygen gas, and/or a compressed gas accumulator. In some embodiments, a portable gas source can be provided that can be worn or accompany a patient. The oxygen source can also be liquid oxygen, or a liquid oxygen generating system.

Gas delivery system or ventilator: The ventilator may provide the main function of gas flow delivery and control. The ventilator may include one or more processors and one or more memories to analyze information, inputs and outputs. When the therapy is being used for respiratory support, the user may have two options: (1) wearing or toting the ventilator module so that the user can be ambulatory or enjoy the activities of daily living, or (2) stationary use, in the event the patient plans on being stationary or does not have the ability to ambulate. The ventilator module may include a display and/or input devices. The ventilator may be wearable as illustrated in FIG. 4, and may include a portable gas source to provide mechanical ventilatory support, or work of breathing support, while being mobile. Conventional ventilators would require the patient to be stationary while receiving ventilatory support, or to use a wheel chair to carry the bulky and heavy equipment that is required for conventional ventilators, and require an encumbering sealing mask and large bore gas delivery tubing.

Gas delivery circuit: The gas delivery circuit delivers the gas from the ventilator to the nasal ventilation mask. It may include a channel to conduct breathing signal and mask ventilation pressure signal between the mask and ventilator. The gas delivery circuit can connect to both sides of the mask, or to only one side of the mask. In the case of NIOV, when being used in stationary applications, the delivery circuit can optionally be provided in a 25-100 foot length, such that the gas source and ventilator module can be stationary in the patient's home, while the patient can move around their home while wearing the interface and receiving the therapy. Or, the gas source can be stationary, and connected to the ventilator module with a 100 foot hose, so that the patient can wear or tote the ventilator and be mobile within the range of the hose. The gas supply tubing can be routed around the ears of the user, or routed in other positions on the user's face, for example, around the corners of the mouth to the front of the neck, in which case a strap may be included to strap the manifold to the face and head. The gas supply tubing may include a channel for delivering gas from the ventilator, and additional lumens, for example, such as a pressure sensing lumen, gas sampling lumen or humidification delivery lumen.

Accessory components: A ventilator module and nasal mask may include or may be in communication with several other functional accessories. A blender can be included to control the fractional delivered O2 in a gas delivery circuit. A pulse oximeter can be used to titrate settings of the ventilator module to meet the physiological needs of the patient, for example setting the correct oxygen blender setting or ventilator volume output. An internal or external humidifier can be included for extended uses of the therapy, or if using in dry climates. The humidifier can be an aerosolization system that produces water particles below 20 microns in size, using a small nozzles, small lumens, interaction with high velocity gas, a vibrating mesh, or combinations of the above, and the humidity delivery system can be a modular component or can be integrated with or into the gas delivery circuit. To prevent rainout from occurring in the nasal interface, the nasal interface may have a drainage line (not shown) to scavenge any moisture that is collecting. A humidification/aerosol injection port is preferably located in a negative pressure zone so that the aerosol can enter the nasal interface. If the humidification/aerosol injection port was in a positive pressure zone, the pressure would prevent the humidified gas or aerosol from entering the nasal interface. Alternately, a heat moisture exchanger (HME) (not shown) may be coupled with exhaled gas exhaust path or entrainment aperture.

A nasal airway pressure sensor is typically included. A transmitter may be included to transmit information regarding the patient, the patient's therapy, and the ventilator performance to a remote location for review, analysis, remote intervention, two-way communication, and archiving. For example, the patient's compliance with the therapy or utilization of the therapy can be monitored and assessed. Important information can be trended, for example the patient's breath rate, I:E ratio, oxygen usage, activity level, or depth of breathing. Also, information can be sent to a ventilator, such as for example, sending programming instructions for setting titration options for the ventilator output to meet the needs of the patient, or sending instructions to the patient. The patient can also send information or questions to a remote clinician through the ventilator and transmitter. As the therapy is frequently used to help ADLs, and to promote activity, a pedometer and/or actigraphy sensor can be included internal to or external to a ventilator module. Optional sensors may include a $CO_2$ sensor, and/or an external breathing sensor unit. A $CO_2$ sensing line and/or an airway pressure sensing line may be present. One or more other external sensors may be included. For example, other external sensors may include an external respiration sensor or respiration effort sensor, such as a respiratory muscle effort sensor, a chest impedance sensor, or other types of sensors, such as a tracheal or other microphone or vibration sensor or acoustical or ultrasonic sensor. The one or more external sensors may be used either as a redundant sensor to a nasal airflow or nasal pressure sensor, or to complement the information obtained from the nasal airflow sensor, or in place of the nasal airflow sensor. An oral airflow breathing sensor may also be used, for example sensor may alternatively be an oral airflow sensor. A drug delivery module can be incorporated internally or externally to a ventilator module. Because of the challenges with current aerosolized drug delivery inhalers, the drug delivery module can be used to propel and deposit medication particles deep in the respiratory system without a carrier propellant. Because the patient using the therapy often may also require prescription medication, this may be a convenient and efficient way to administer the medication.

The nasal ventilation mask: As previously noted, the nasal ventilation mask of the invention can be used in both NIOV applications and NIV applications.

In the case of NIOV, ventilation gas may exit at a speed that entrains ambient air, such that the combination of ventilation gas, entrained ambient air and spontaneously inhaled air, if the patient is spontaneously breathing, is delivered to the patient's airways, such as the nasal cavity, oropharyngeal airway, trachea, lung and others, under power to create a clinically efficacious effect on the lung and airways. The patient may exhale through the nose or mouth. When using the invention in conjunction with NIOV, the patient breathes normally through their upper airway and through their nose, while receiving mechanical support through the interface. During exhalation, the exhaled gas preferably does not enter the gas delivery circuit but rather exits the nose or mouth directly to ambient air, or through, across or around the nasal interface to ambient air. The patient can keep their mouth closed during use for example during inspiration, to help direct the mechanical support to the lower airways or can use a mouth guard or chin band, if necessary. The patient may exhale through their mouth when using the therapy. Details of the Venturi function of the NIOV mask are explained later and explained in detail in U.S. Patent Application No. 2010/047921, which is incorporated by reference in its entirety.

FIGS. 5-23 describe embodiments of the nasal mask with a nasal sealing cushion, manifold and gas delivery tubing arrangement.

Figure 17:
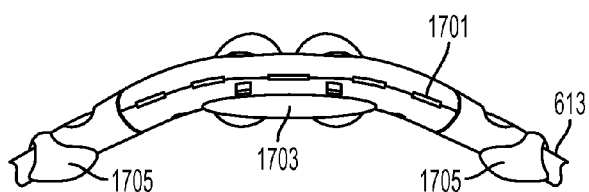
FIG. 17 shows a bottom view of the nasal ventilation mask including skin cushions.
Figure 18:
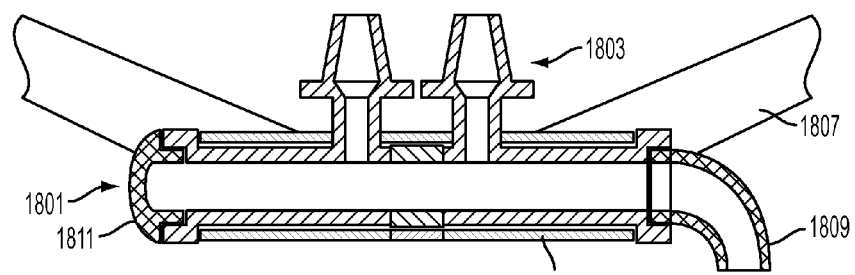
FIG. 18 describes a cross-section through the flow path of a nasal ventilation mask of the present invention directed toward NIV.

FIGS. 5-17, and 19-23 describe exemplary embodiments of the invention used in conjunction with a NIOV mask, FIG. 18 describes an exemplary embodiment of the invention used in conjunction with an NIV mask.

Figure 5:
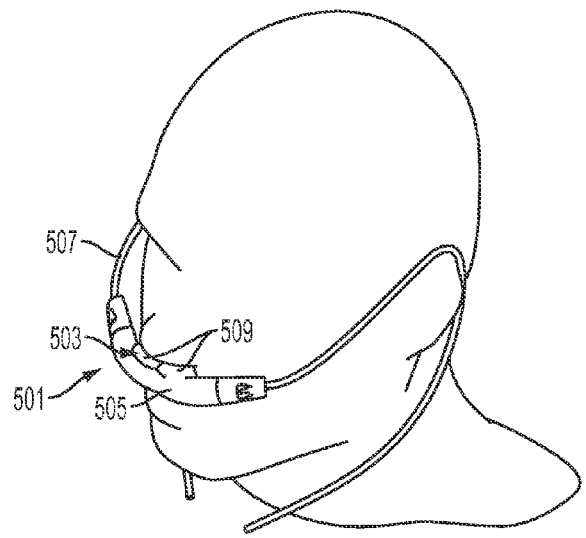
FIG. 5 shows an exemplary embodiment of a nasal ventilation mask where an open, non-sealing nasal mask may be curved and configured to be placed under the nose of the user, and which may extend bilaterally from the midline of the face to the sides of the nose.

FIG. 5 describes an exemplary nasal mask 501 being worn on a person's face, showing a nasal sealing cushion assembly 503, a manifold 505, and a gas delivery circuit 507. The nasal sealing cushion assembly 503 may have one or more nasal connectors 509. As used in the specification, the term "nasal connector" may include nasal pillows or cushions, barbs, sleeves, cannulas, and other devices that deliver gas from a gas source to a patient's nose or nasal airways. For illustrative purposes only, the figures and written description refer to nasal pillows; however, it is understood that any reference to a nasal pillow could similarly refer to any type of nasal connector. The one or more individual pillows or cushions 509 may be fluidly coupled to the compliant inner tube. Alternatively, the one or more individual pillows or cushions 509 may be attached directly to the manifold 505. The nasal sealing cushion assembly 503 may be compliant. The manifold 505 may be rigid or semi-rigid, but could also be compliant or malleable, or a composite combination of soft and rigid sections.

Figure 6:
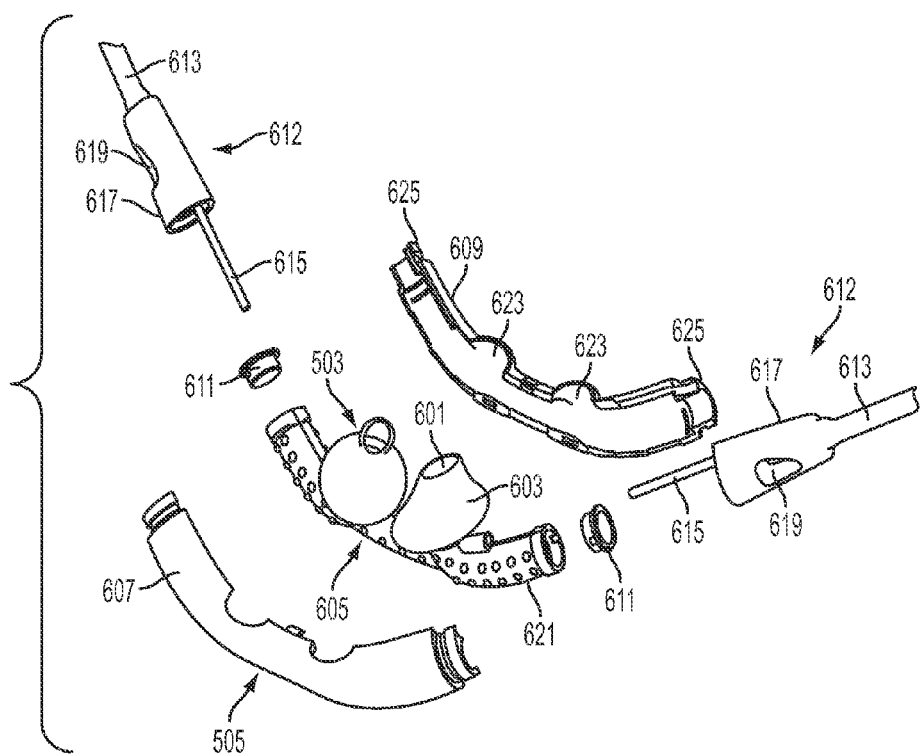
FIG. 6 shows an exploded view of the nasal ventilation mask of FIG. 5.
Figure 7:
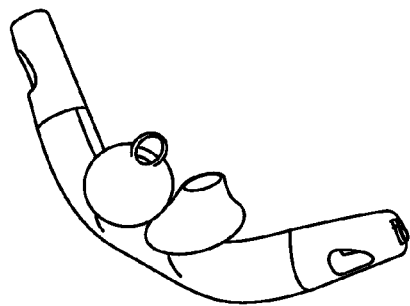
FIG. 7 shows a front isometric view of the nasal ventilation mask of FIG. 5.
Figure 9:
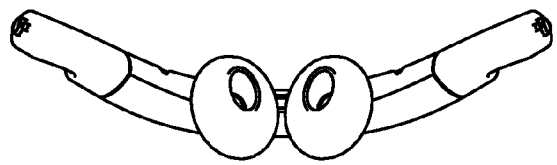
FIG. 9 shows a top view of the nasal ventilation mask of FIG. 5.

The nasal sealing cushion assembly 503 may include an offset concentric configuration in which the perimeter and center of the distal end opening 601 is nonconcentric to the perimeter and center of the base 603 of the each pillow 509, as shown in FIGS. 6, 7 and 9. The offset perimeter and center of the distal end opening 601 may allow the mask 501 to have a universal dimension of the manifold 505 from a center point of the base 603 of a first pillow to a center point of the base 603 of a second pillow. This may be accomplished by biasing the distal end openings 601 of the pillows 509 toward or away from the midline of the manifold 505, while allowing the pillows 509 to avoid interfering with each other at the wide dimension of the base 603 of the pillows 509.

The nasal pillows 509 may impinge on a rim of the nostril, seal on the rim of the nostril, seal inside the nostril, impinge on the tissue underneath the nose, or various combinations of the above. The nasal pillows 509 may typically be soft and compliant to allow for comfortable contact with the nostril and, if a seal is intended, compress against the nostril in a comfortable manner. The nasal pillows 509 may typically include convolutions in the shape to allow the extension to flex in multiple planes, and to compresses along a centerline axis, to conform to the user's nose. The nasal pillows 509 can seal against the nostril rim or other part of the nostril so that there is not inadvertent leakage between the nasal pillows 509 and nose and so that the majority of the breathing gas flows through the nasal pillows 509. However, this seal does not need to be leak free, and in some embodiments the may be a desired gas flow between the nasal pillows 509 and the nostril. The nasal pillows 509 can be permanently affixed to the nasal interface or can be removably attached. The nasal pillows 509 may be available in different sizes so that the user can select a size that matches their anatomy.

FIG. 6 illustrates an exploded view of the nasal ventilation mask 501 of FIG. 5, which may include a combined nasal sealing cushion assembly and an inner tube (NSCAIT) assembly 605. The NSCAIT assembly may be made of a compliant material, such as, for example, silicone rubber or other similar materials. The compliant material may allow for molding of complex shapes that are not manufacturable in mass with harder materials.

The manifold 505 of FIG. 5 may be a multi-part assembly that may include a front piece 607 and back piece 609, which snap together around the NSCAIT assembly 605, snap rings or inner tube retaining rings 611 to position and secure the NSCAIT assembly 605 into the manifold 505, and a gas delivery circuit assembly 612.

The retaining rings 611 may add rigidity to proximal ends of NSCAIT assembly 605 and/or may assist the NSCAIT assembly 605 in holding its shape. The retaining rings 611 may provide the only attachment of the NSCAIT assembly 605 to the manifold 505 in certain embodiments, allowing for movement of the NSCAIT assembly 605 within the manifold 505 for positioning or other purposes. In certain embodiments, the NSCAIT assembly 605 may slide over a portion of the retaining rings 611 prior to the retaining rings 611 being captured between or within the manifold 505.

Figure 15:
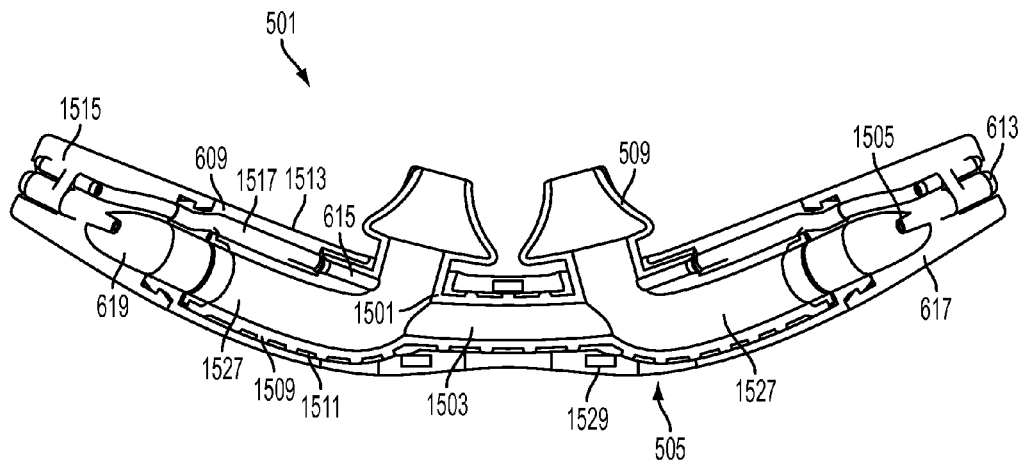
FIG. 15 shows a front view of a cross section view through the flow path of nasal ventilation mask of FIG. 12 along line A-A.

The gas delivery circuit assembly 612 may include a sensing extension tube 615, a manifold attachment hub or gas delivery circuit connection 617, and gas delivery tubing 613. Other features may include an entrainment port 619 and/or a nozzle 1505 for NIOV, as shown in FIG. 15.

One or more entrainment ports 619 may be used. Preferably, dual entrainment ports may be used to reduce risk of a blockage during side sleeping by a user. For example, if a first entrainment is blocked by the user's position during sleep, the second entrainment port may still be exposed to ambient air and may allow for proper ventilation treatment of the user. Although two entrainment ports are shown, other embodiments with more or fewer entrainment ports are contemplated. One or more entrainment ports 619 may be located on each side of the manifold 505.

The NSCAIT assembly 605 may include one or more nasal sealing cushions 509 at a distal end and/or a gas flow tube 621 at a proximal end. The NSCAIT assembly 605 may be constructed with a compliant material. The nasal pillows 509 may be formed as one piece with the compliant tube 621, and/or may not include any joints. The nasal sealing cushion assembly 503 may include one or more nasal pillows 509 at the superior or distal end, where the nasal pillows 509 impinge with an individual nostril and compress as necessary.

A stem 1501 (See FIGS. 15 and 16) of each of the one or more nasal pillows 509, just below the widening of the nasal pillow 509, can flex in any direction 360 degrees along its circumference, allowing the nasal pillows 509 to be aligned with the nostrils. As described later, the flex or gimbaling zone of the stem 1501 may extend to below the superior or top surface of the manifold 505.

The NSCAIT assembly 605 typically includes a non-angulated flow path that is generously radiused to facilitate laminar and low resistance flow. The NSCAIT assembly 605 may include an interconnection lumen 1503 (See FIGS. 15 and 16) between the left and right side to balance pressure between the left and right nasal airways or to shut flow to the least resistive nostril. This may provide additional safety for the user in the case that one nostril is blocked. The interconnection lumen 1503 may provide for a smaller and symmetrical device.

Figure 21A:
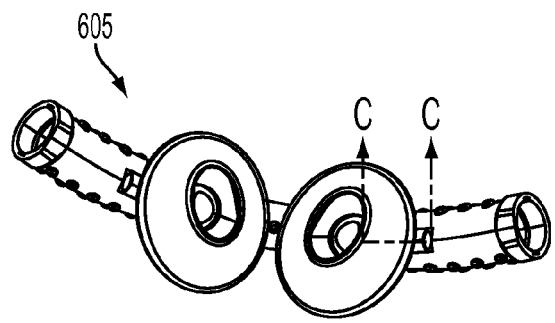
FIG. 21A-21C show an exemplary embodiment of a nasal sealing cushion assembly and an inner tube assembly with a flow dampener.
Figure 21B:
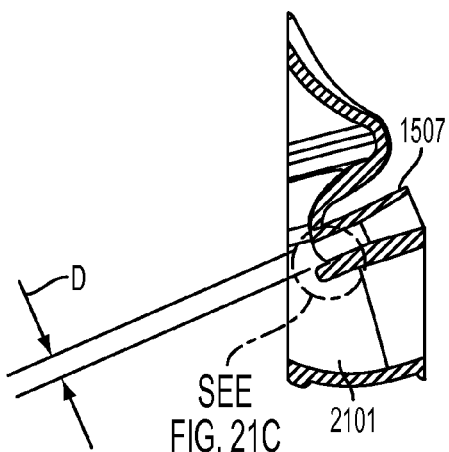
Figure 21C:
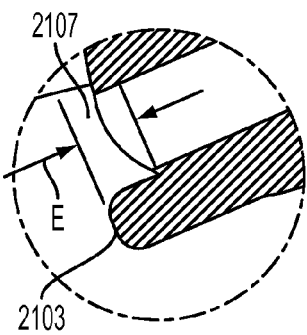

The NSCAIT assembly 605 may also include a breathing pressure and mask ventilation pressure sensing port 1507 at or near the nasal cushion area. The sensing port 1507 may be located anywhere on the nasal interface device 501. Preferably, the sensing port 1507 may be located in close proximity to the nose, such as in the nose, on a jacket, at the entrance to the nose, at or near the pillows 509, at or near a base of the pillows 603, at or near the stem 1501, or at other locations within the nasal interface device 501. FIG. 21A shows an exemplary NSCAIT assembly 605. FIG. 21B shows a cross section along section C-C of FIG. 21A. As shown in FIG. 21B, the sensing port may enter the main gas pathway 2101 approximately at the turn from a substantially horizontal flow to a substantially vertical flow. Other locations may be used. The sensing port 1507 may have a decreasing, increasing, constant or variable profile prior to connecting with the main gas pathway 2101. In a preferred embodiment, the width "D" of the distal opening 2107 of the sensing port 1507 may be between about 0.01 to about 0.2 inches, more preferably, between about 0.04 to about 0.10 inches, and most preferably about 0.06 inches.

The NSCAIT assembly 605 may also include a sensing system/flow dampener feature 2103 (See FIGS. 21A-21C) near the sensing port 1507 to differentiate inspiratory versus expiratory signals occurring within the NSCAIT assembly 605. The flow dampener feature may include a protrusion 2103 on one side of the distal opening 2107. The protrusion 2103 may be located on a proximal side of the sensing port 1507, wherein pressure created at the sensing port 1507 increases for patient expiratory flow and decreases for patient inspiratory flow. Alternatively, the protrusion may be located on a distal side of the sensing port 1507, wherein pressure created at the sensing port 1507 decreases for patient expiratory flow and increases for patient inspiratory flow. The protrusion 2103 may extend a distance "E" of about 0.01 to about 0.2 inches into the main gas pathway 2101, more preferably about 0.02 to about 0.1 inches, more preferably about 0.03 to about 0.06, and more preferably about 0.04 inches.

The sensing port 1507 may receive a pneumatic pressure sensing tube or lumen or another form of sensor. In certain embodiments, two sensors are used, one for each nostril/each of the left and right gas flow paths. This may be beneficial in the event that one nostril becomes blocked. In certain embodiments, the sensing lumens may be tied together along a gas delivery circuit, such as after the tubing passes over the ears and meets under the user's neck.

The gas flow tube portion 621 of the NSCAIT assembly 605 may include, on its outer surface, bumps or protrusions 1509 (See FIGS. 15 and 16), which may be used to create a space 1511 between the NSCAIT assembly 605 and inner walls of the manifold 505, including the front piece 607 and back piece 609 in a multi-piece manifold.

As described, the manifold 505 may include multiple pieces. As shown in FIG. 6, the manifold 505 may include a front piece 607 and back piece 609. The manifold 505, when assembled, may have a compound arcuate shape that is most advantageous to mate with the facial anatomy. Alternatively, the manifold may be substantially straight or may have a substantially straight interior configuration.

The manifold 505 and/or the NSCAIT assembly 605 may have compound arcuate curves, either separately or in combination. The NSCAIT assembly 605 may be substantially straight in a relaxed state, but the manifold 505 may have compound arcuate curves. In this situation, the NSCAIT assembly 605 may adopt the compound arcuate curves of the interior of the manifold 505 because the NSCAIT assembly 605 may be compliant.

The manifold 505 and/or the NSCAIT assembly 605 may be shaped with compound arcuate curves, and can curve from the midline laterally, posteriorly and superiorly, as shown in the example of FIG. 6. The manifold 505 and/or the NSCAIT assembly 605 can curve in other directions as well, such as inferiorly. The compound arcuate curves may allow for the manifold 505 and/or the NSCAIT assembly 605 to tightly wrap around an individual's face to achieve a user's perception of minimal size, user comfort and improved sealing. User comfort may be improved by having the soft nasal pillows be the only element touching the user's face, as compared to nasal cannulas that have stiffer material inside the user's nose and across the user's cheeks or headgear to retain an interface against the user's face. Improved sealing may be achieved by having a compound arcuate shape and wrapping gas delivery circuit tubing around the user's ears. Any retaining force created by wrapping around the user's ears is then exclusively used to hold the nasal pillows against the nose, rather than applying some force to the cheeks, and creating a better seal without a significant additional amount of force placed on the ears or nose. The manifold 505 may be rigid or semi-rigid to provide a superstructure around the NSCAIT assembly 605 to preserve the integrity of the gas flow path dimensions and patency.

The compound arcuate curves of the manifold and/or the NSCAIT assembly 605 may provide a smooth, uninterrupted gas flow path from the entrainment ports 619 to the distal openings of the pillows 509. There may be a smooth, but rapid turn from the nose and pillows 509 in a substantially vertical direction to a substantially straight lateral direction or horizontal without any corners. There may also be smooth turns in the posterior and superior directions. The gas flow path within the manifold 505 may be substantially straight, but still curves posteriorly around the user's face to maintain a low profile. A superior turn may be in the direction up towards the ears to direct a retaining force.

The manifold 505 may include an opening near its midline, or in the example shown in FIG. 6, two separate openings 623 to the left and right of the midline, through which the nasal pillows 509 of the NSCAIT assembly 605 may protrude superiorly. The manifold 505 may include weep holes or drain holes 1701 (See FIG. 17) to drain fluids that may collect. The gas delivery circuit connection 617 can be removably connected to the proximal ends 625 of the manifold 505 and be used to snap the manifold pieces 607, 609 together around the NSCAIT assembly 605. This may enable easy assembly, disassembly, cleaning, and replacing of the NSCAIT assembly 605, including changing sizes of the NSCAIT assembly 605 to ensure proper sizing for a particular patient. The gas delivery circuit 613 can be attached to both or just one side of the manifold 505. The gas delivery circuit connection 617 can be a rotational locking connection, an interference locking connection, and/or a keyed locking connection.

Traditional fabrication of a curved nasal ventilation mask has several challenges that the present invention may solve. Specifically, a semi-rigid manifold 505 is preferred to provide structural integrity to a mask. It is highly preferred that the manifold 505 include compound curves for form, fit and function. The curves, however, are difficult and/or expensive to fabricate because of the non-straight geometry. If the manifold 505 is fabricated in multiple pieces for ease of fabrication, such as ease of molding, then the multiple pieces must be joined in a manner that seals the pieces together to prevent air leaks, for example. However, this then also increases complexity, cost and the potential for unreliability. In the present invention, this problem may be solved by making the semi-rigid manifold an outer frame only. Instead of relying only on a rigid manifold, an internal compliant compound curved inner tube is placed inside the manifold. The inner tube may now define the leak free gas flow path, not the manifold. In embodiments of the present invention, the manifold 505 may be a superstructure to simply hold the inner tube 605 in place. The inner tube 605 can be fabricated easily because of its compliant nature. The manifold 505 can be made out of multiple pieces that are joined without need to seal the joints since the manifold 505 is not being relied on to define the gas flow path. As the gas flow path is through the inner tube 605, gas leaks through the manifold 505 are not a concern. As such, the result is a leak free, easy to manufacture design that has an optimal curved shape.

Nasal ventilation masks that employ pillows-type sealing cushions to seal with the nostrils have several challenges that embodiments of the present invention may solve. Specifically, attaching a compliant nasal sealing cushion to the top of a rigid or semi-rigid manifold requires a joint or connection between the two pieces, which limits gimbaling or pivoting. The necessary amount of gimbaling or pivoting can be achieved by increasing the length that the pillows extend from the manifold, to provide a zone along the length of the pillow where the pillow can pivot. However, this adds to the length of the pillow, and therefore the size and obtrusiveness to the overall mask. Therefore, the manifold must be positioned further away from the nostrils, closer to the mouth. This in turn results in an overall larger and more obtrusive configuration. Also, the required snap fit or joint between the cushion and the top of the manifold increases cost and complexity, and can affect reliability. In embodiments of the present invention, this problem is solved by not connecting the nasal cushion to the top of the manifold, but rather extending the nasal cushion 509 into the manifold 505 and securing the two together inside the manifold, for example by concentric interference 1501 within the manifold 505, as shown in FIG. 15. This arrangement may eliminate the joint, thus, improving cost, complexity and reliability, and improves gimbaling because of the absence of the joint, which is effectively eliminated. The gimbaling zone of the nasal pillow 509 may be moved to below a top surface 1513 of the manifold 505, thus increasing gimbaling without increasing the distance between the nose and the manifold, and providing increased gimbaling in the smallest possible footprint. Alternatively, the nasal cushion 509 and the inner tube 605 may be continuous and/or formed from a single piece of material (See FIGS. 15 and 16).

Nasal ventilation masks that include both gas delivery and breath sensing functionality can be complicated and expensive to manufacture. This problem may be solved in embodiments of the present invention by having two main subassemblies. A first subassembly may include a gas delivery port or in the case of NIOV a gas delivery nozzle 1505, the gas delivery tubing 613, and breathing pressure sensing line 1515, a pressure sensing extension tube 615, and a connection to the second subassembly. A second subassembly may include a manifold 505, a gas delivery tube 621, nasal sealing cushion 509, a sensing tube extension guideway 1517, and breathing pressure sensing port 1507. The subassemblies are configured such that the extension tube 615 of the first assembly engages with the sensing port 1507 in the second assembly, and such that the first subassembly can be easily and optionally removably connected to the second subassembly. The later provides easy assembly, facilitates easy disassembly for cleaning and or replacement of components, or for different sizing options; for example, different length gas delivery circuits, or different size nasal sealing cushions.

Nasal ventilation masks that include compound arcuate shapes can have the disadvantage of possessing corners or places within the gas flow path where mucus, debris or germs can collect. The problem may be solved in the present invention by employing the NSCAIT assembly 605 as the principle gas flow path. The NSCAIT assembly 605 may be fabricated such that it is completely or nearly completely free of pockets or corners that could collect debris. The smooth gas flow path also makes cleaning easier and more effective. Further, because the nasal ventilation mask manifold 505 is a superstructure and does not need to seal, it can be designed to easily be disassembled, such that the other components, for example the NSCAIT assembly 605, can be removed from the overall assembly for cleaning, replacement, or size selection.

Overall cross sectional geometry of the manifold 505 can be generally round, semi-round, D-shaped, oval or variable to optimize performance and ergonomics. The cross-sectional area can be variable, variably increasing from proximal to distal, and/or constant. Flatter cross sectional geometries that do not protrude far from the user's skin may be configured ergonomically. The internal structure of the manifold may be devoid of corners and abrupt bends and angles to facilitate efficient gas flow fluid dynamics and sound generation. An abrupt bend or angle may be a bend or angle other than approximately 90 degrees, preferably 120-150 degrees. The manifold may be made of a semi-rigid material, either a thermoplastic or elastomeric material, typically of 30-60 Shore A hardness in applications in which the manifold is desired to be flexible, and 60-90 Shore A hardness in applications in which the manifold is desired to be rigid or semi-rigid. The manifold can also be constructed of both semi-rigid or rigid and flexible materials, for example a rigid construction for the gas flow path and/or sensing lumen portions. A soft flexible material may be found at one or more flex points, or surrounding the gas flow path and/or sensing lumen portions. Alternatively, the skin or posterior side of the manifold can be soft and flexible, while the anterior side of the manifold can be rigid or semi-rigid. The manifold can also be constructed to be malleable or moldable by the user for the user to make minor adjustments to allow the nasal interface to fit ideally to that individual. The overall nasal interface can be disassemble-able, so the user can take the assembly apart for cleaning, or to assemble correct sizes of the different parts together to customize the fit. The manifold and nasal cushions, if included, may typically be translucent, but also can be transparent or opaque. The gas flow path geometry can be round in cross section or can be non-round, such as D-shaped, oval, or elliptical, in order to optimize both flow dynamics, sound and ergonomics. The gas flow path in the manifold may be dimensioned such that the patient can breathe freely through the gas flow path without feeling restricted. Typically, the gas flow path and Venturi are configured so that positive pressure is developed in the gas flow path before the gas flow path curves superiorly toward the distal end gas flow opening. The gas flow path may be curved and devoid of abrupt angles and corners to channel the gas with as little resistance and disturbance as possible, and so that the gas being delivered by the gas delivery jet nozzles flows in an organized flow profile with minimal turbulence.

The mask may be configured to curve from the nose laterally and posteriorly away from the nose, which positions the components of the mask lateral to the nose, which makes the mask as unobtrusive as possible. The mask therefore does not hinder speaking or eating, and is away from the line of sight. The manifold may be typically shaped in a compound arcuate shape to match the contours of the face under and to the side of the nose. The manifold may typically curve bilaterally and posteriorly. The manifold can also curve superiorly or inferiorly as it is curving laterally and posteriorly. The mask can be a bilateral assembly meaning gas delivery tubing is attached to both the left and right side, or it can be unilateral meaning that the gas delivery tubing is attached to only one side. The later configuration may be useful for side sleeping or to reduce the obtrusiveness on one side of the face.

Figure 8:
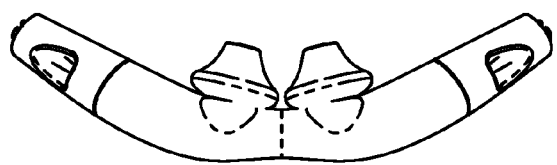
FIG. 8 shows a front view of the nasal ventilation mask of FIG. 5.
Figure 10:
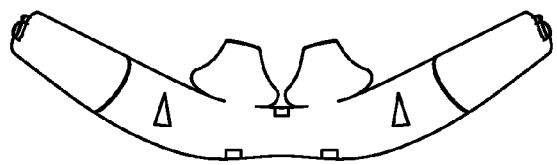
FIG. 10 shows a rear view of the nasal ventilation mask of FIG. 5.
Figure 11:
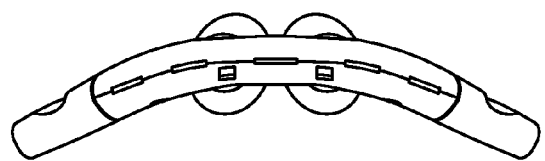
FIG. 11 shows a bottom view of the nasal ventilation mask of FIG. 5.
Figure 12:
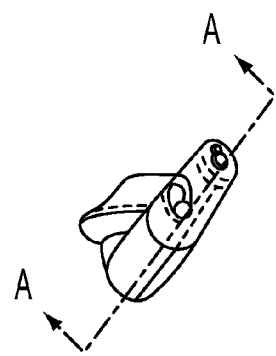
FIG. 12 shows a side view of the nasal ventilation mask of FIG. 5.
Figure 13:
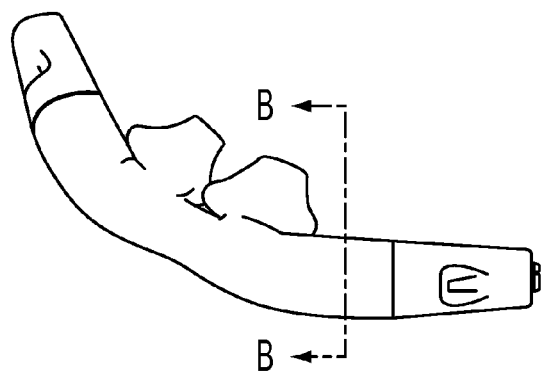
FIG. 13 shows a front isometric view of the nasal ventilation mask of FIG. 5.
Figure 14:
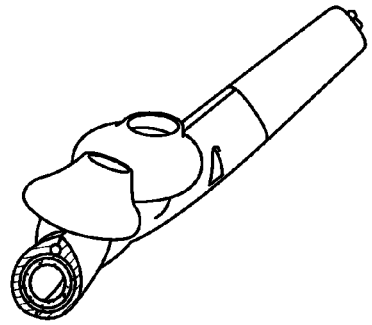
FIG. 14 shows a cross-sectional side view of the nasal ventilation mask of FIG. 13 along line B-B.

FIGS. 7-23 show different views of the nasal ventilation mask of the present invention. FIG. 7 shows a front isometric view; FIG. 8 shows a top view; FIG. 9 shows a front view; FIG. 10 shows a posterior view; FIG. 11 shows a bottom view; FIG. 12 shows a side view; FIG. 13 shows a front-side view; FIG. 14 shows a cross-sectional view through Line B-B of FIG. 13, showing the gas flow path, a gap between the manifold and the inner tube and weep holes in the manifold for moisture drainage out of the manifold.

Figure 16:
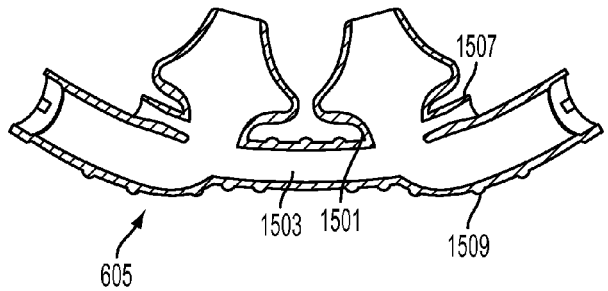
FIG. 16 shows a cross sectional view of the nasal cushion and inner tube assembly shown in FIG. 15.

FIG. 15 shows a cross-sectional view of the nasal ventilation mask assembly 501 through the gas flow path. The NSCAIT assembly 605 may be placed inside the manifold 505, between the manifold back piece 609 and the manifold front piece 607. The sensing extension tube 615 may extend through the guideway 1517 inside the manifold 505 from the proximal end to a sensing port 1507 placed in a stem section 1501 of the pillows 509. A sensing port 1507 may be included, as well as an interconnecting channel 1503 between multiple gas flow paths, when a main gas pathway 1527 is divided into two or more pathways, such as a left and a right gas pathway. The term "main gas pathway" 1527 may be used to refer to a path for gas through the inner compliant tube, either as one single pathway, such as from an entrainment port to an exit from a nasal pillow, or as multiple pathways, such as from the left side and the right side from respective entrainment ports to respective exits from respective nasal pillows. One or more snaps 1529 may attach the various pieces of the manifold 505. A nasal sealing cushion may have a pillow section 509 and a stem 1501. A gas delivery nozzle 1505 may provide gas in the case of NIOV. FIG. 16 shows a cross-sectional view of just the nasal cushion and inner tube assembly portion of FIG. 15.

FIG. 17 shows a bottom view of an alternate embodiment of the nasal ventilation mask in which the skin side of the manifold 505 includes a skin pad or cushion 1703, which helps set the correct distance between the manifold and the face, helps set the proper angle of the pillows in the sagittal plane so that the pillows are aligned with the nares, helps absorb strapping forces so that the mask can be strapped to the user without discomfort, and helps secure the mask by preventing it from slipping. FIG. 17 also shows skin cushions 1705 near the proximal end of the manifold assembly, which also serve to absorb strapping forces and secure the mask to the face and preventing it from slipping.

FIG. 18 shows a cross-sectional view of the nasal ventilation mask 1801 with an NIV embodiment. As described previously, the nasal sealing cushion and inner tube assembly 1803 is surrounded by a manifold 1805. In the example shown, the mask may be secured to the face by a head strap 1807, although it can be secured to the face with the gas delivery tubing or a combination of the gas delivery tubing and a strap. In the example shown, the gas delivery circuit 1809 attaches to one, not two, sides of the manifold assembly, which may be preferred in some applications such as sleeping as this configuration allows one side of the face to be absent of tubing. In this case, the opposite side of the manifold assembly may be capped 1811. Unilateral gas supply attachment is exemplary only, and the mask can be used with the gas supply attached to both sides.

Figure 19:
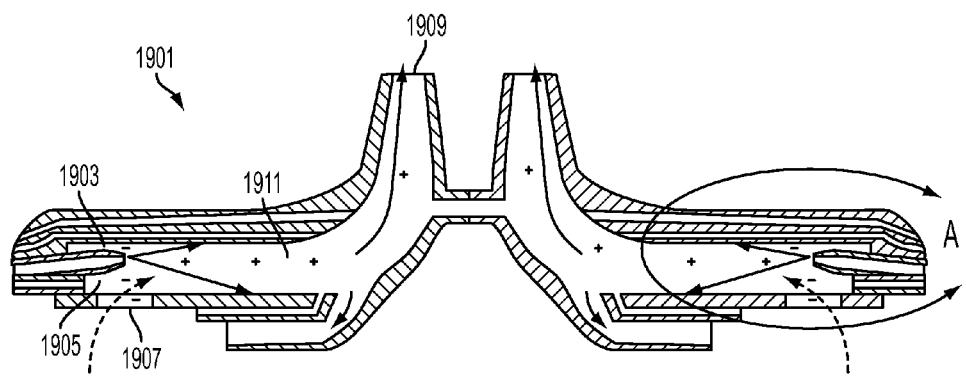
FIG. 19 describes a cross-section through the flow path of a nasal ventilation mask of the present invention directed toward NIOV.
Figure 20:
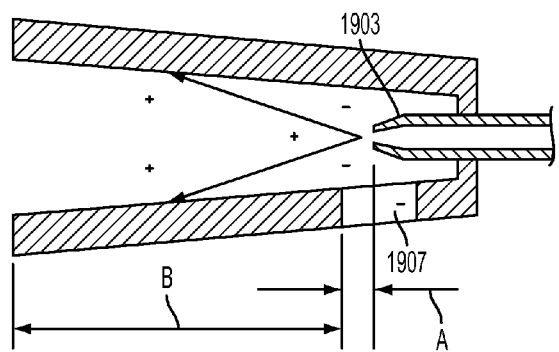
FIG. 20 describes the dimensional relationships of the nasal ventilation mask of FIG. 19 at area A.

FIG. 19 shows a cross-sectional view of the nasal ventilation mask 1901 when used in conjunction with the NIOV embodiment. FIG. 20 shows a cross-sectional view of the area shown in detail A of FIG. 19. The gas exiting the gas delivery jet nozzles 1903 within the gas flow path may create a negative pressure area 1905 at and/or near the entrainment apertures. The negative pressure may draw ambient air into the gas flow path through the entrainment apertures 1907. Preferably, at least a portion of the entrainment apertures are located between the gas delivery jet nozzles 1903 and the distal end gas flow openings 1909. This unique Venturi configuration may allow a negative pressure region to form in the gas flow path just inside the entrainment apertures while forming a positive pressure region 1911 between the entrainment apertures and the distal end gas openings. When gas is emitting from the nozzles 1903, this gas creates a cone-shaped flow or velocity profile. Typically, as will be explained in more detail subsequently, the area within this cone is positive pressure and the area outside of this cone is negative pressure. Typically, when the cone intersects with the internal walls of the manifold gas flow path, the entire area distal to that intersecting point will be under positive pressure. Typically, the nasal interface permits the user to breathe ambient air freely in and out of the manifold, through the entrainment apertures. Alternatively, the user may breathe ambient air at least partially in and out of separate spontaneous breathing ports, which may be separate from the entrainment apertures and positioned elsewhere along the gas flow path of the manifold. The entrainment apertures may be single apertures or multiple apertures and the spontaneous breathing ports, if present and separate from the entrainment apertures, may be single ports or multiple ports. In certain embodiments, the spontaneous breathing ports can be roughly or substantially in-line with the distal end gas flow openings. Alternatively, the spontaneous breathing ports can be located on a superior, inferior, or anterior surface of the manifold, or a combination of these surfaces. In general, the spontaneous breathing ports are preferably placed so that exhaled gas from the patient is directed in a natural velocity and or direction, so it does not irritate the users. The unique Venturi system achieves relatively high levels of ventilatory support with relatively small amounts of delivered gas, making it possible for the ventilator, gas source and gas delivery circuit to be miniaturized, thus making ambulation with the system convenient, discrete and easy. The patient can inhale and exhale ambient air directly through the mask while receiving ventilatory support, in which there is negligible dead space volume in the mask, allowing the patient to feel and act normally while receiving the therapy. For example, the patient can talk, swallow, eat or drink, and feel like they are breathing normally, while receiving the therapy.

The entrainment apertures are preferably located near tips of the gas delivery jet nozzles, but can be placed in other locations on the manifold as well. In certain embodiments, the tips of the gas delivery jet nozzles can be completely proximal to the entrainment aperture. In other embodiments, the tips may be approximately flush with a proximal end of the entrainment aperture, between a distal end and the proximal end of the entrainment aperture, or approximately flush with the distal end of the entrainment aperture. The entrainment apertures can be positioned near the lateral proximal ends of the manifold, and can be on the superior, anterior, inferior surfaces of the manifold or combinations thereof. In contrast, typical jet pump systems position a nozzle distal and/or concentric to an entrainment port. The proximal positioning of the gas delivery jet nozzle in the present invention preferably allows flow inside the manifold to develop into positive pressure laminar flow in the shortest possible length or distance, which preferably minimizes obtrusiveness, which is a significant advantage. It is a significant advantage to develop laminar positive pressure flow within the manifold prior to the gas entering the patient. Turbulent flow entering the nose is uncomfortable to the patient. Typical jet pumps are not concerned with generating positive pressure laminar flow within the jet pump area, rather the aim of a jet pump is to maximize the pressure exiting the jet pump area. Turbulent flow, if entering the patient, would include vortices and velocities that would create shearing effects that would increase noise and boundary effects that would irritate the nasal tissue. The laminar flow generated by the present invention will smooth out the flow profile, such that vortices and velocity profiles are more uniform, reducing the noise and irritation to a level acceptable for the application. For example, turbulent flow may include localized velocity currents that are greater than 300 lpm, whereas the laminar flow of the invention may produce a maximum localized velocity current of less than 200 lpm, based on nominal conditions.

The entrainment apertures can be variably adjusting. For example, the entrainment apertures can be adjusted between fully open and fully closed. The adjustment can control the level of ventilatory support to the desired level that the overall system is intended to provide for the prevailing situation. The adjustment can be manual, but is preferably automatic with the use of valves, for example a valve that is controlled by a pressure signal delivered from the ventilator though a small bore conduit to the valve. Alternatively, the position of the gas delivery jet nozzles relative to the entrainment apertures can be adjusted by a slide mechanism, either manually or automatically. The level of support can range from partial support to full ventilator support. The gas delivery nozzle may be proximal to the entrainment port, or the gas delivery nozzle may be proximal to at least a portion of the entrainment aperture.

In certain embodiments of the present invention, the gas flow path cross sectional area may not reduce between the entrainment aperture and the distal end of the gas flow path, whereas typical jet pump systems include a reduction in cross section, which increases pressure output but decreases flow rate throughput, which would be undesirable in a medical ventilation application. The substantially uniform or optionally increasing cross sectional area between the proximal and distal ends of the gas flow path, may maximize the flow rate capable of being delivered by the system into the patient, and also reduces the inhalation and exhalation resistance through the manifold. In alternative embodiments, the gas delivery jet nozzles can be positioned in the manifold near the base of nasal cushions, inside the nasal cushions, or in the manifold at any distance proximal to the nasal cushions.

It may be desirable to measure pressure being delivered to the patient, which can be done by sensing the pressure in the manifold in a positive pressure zone using a pressure sensing lumen terminating at a sensing port in the positive pressure zone, shown in FIG. 19. The pressure inside the manifold may be measured to detect the breathing of the patient, determine the phases of breathing, patient status, and time the delivery of the ventilation gas as appropriate, as well as for monitoring of the patient and ventilation pressure for alarm and control system purposes. The pressure inside the manifold may be measured continuously by a transducer in a ventilator by a conduit connecting the pressure tap to the transducer. Ideally, the pressure tap may terminate at a point in the gas flow path that has as few artifacts as possible, which is typically as close as possible to the distal end gas flow openings. The pressure taps may typically include the pressure sensing port and a sensing lumen that extends back to the ventilator and is in communication with the ventilator control system.

One or more other respiration sensors may be located inside the manifold or on a surface of the manifold. The one or more other respiration sensors may be positioned in a location that is minimally affected by artifacts caused by the gas delivery jet nozzles, such as a vacuum signal. The one or more other respiration sensors can be other types of sensors, such as thermal, sound, vibration, gas composition, humidity, and force, or any combination thereof. The one or more other respiration sensors can be used to measure breathing pressures, but can also be used to measure breathing gas flows, or other breath-related parameters, such as sound or gas composition. There may be a combination of respiration sensors inside the manifold and/or one or more respiration sensors on the outside of the manifold. The respiration sensors can be integral to the manifold, or located remotely from the nasal interface in a ventilator (not shown). There may be two breath sensors, one for each nostril, or a single breath sensor. There may be multiple respiration sensors for a nostril, for example, an inspiratory breath sensor, and an expiratory breath sensor. The sensors can also be used to measure gas flow and gas volume, for example inspired and expired flow rate and inspired and expired tidal volume, of both the ventilator delivered gas and the spontaneously breathed gas. In addition to breath sensing, the apparatus may also include gas composition sensors, such as end-tidal $CO_2$ sensors, and oxygen sensors. $CO_2$ is a useful clinical parameter to measure and respond to, and can also be used as an additional breath detector, apnea detector, leak detector, and interface fitting detector (a certain characteristic $CO_2$ signal may indicate proper or improper fitting and placement of the interface). Oxygen may be a useful parameter to measure and can be used to determine the $FIO_2$ being delivered by the system to the patient and therefore can be used as a measured parameter and to make ventilator adjustments to achieve the desired $FIO_2$.

In an alternate embodiment, the manifold and the gas flow path can also include a secondary channel, an exhaust flow path, used to divide the flows of exhaled gas exiting the patient and gas being delivered to the patient by the mask. Dividing these paths may significantly reduce shearing that occurs when gases are simultaneously exiting and being delivered to the patient, when these gas flows share a common path. The reduction in shearing leads to a reduction in sound generated by the system, which is a significant advantage in the applications intended by the invention, such as mobile ventilatory support, and sleep disordered breathing. When the exhaust path is included, the exhaust path may permit the patient to inspire through the exhaust path in addition to inspiring through the spontaneous breathing aperture. The total gas inspired by the patient may be a combination of (1) supplemental ventilation gas being delivered from a ventilator through the gas delivery jet nozzles, (2) entrained air drawn through the entrainment apertures by the ventilation gas exiting the gas delivery jet nozzles, and (3) air drawn through the entrainment apertures or spontaneous breathing ports from the patient's own spontaneous breathing effort. Exhaled gas may be exhaled entirely through the entrainment apertures, through other ports in the manifold, through the patient's mouth, or any combination thereof.

The gas delivery jet nozzle directional alignment may be aligned with the average centerline arc of the internal gas flow path geometry of the manifold in applications in which pressure generation is more important than minimizing sound. In alternate embodiments as shown, when minimizing sound generation is more important however, the gas delivery jet nozzles can be angled away from a centerline and can be off-center which reduces sound generation but reduces pressure output generation. In the mobile ventilation application, a balance in the sound and pressure generated by the device is achieved by placing the gas delivery jet nozzle at a 10-30 degree angle to centerline, and 5-25% off center, which can result in a sound level of 40-60 dB and a maximum pressure output of 12-35 $cmH_2O$.

FIG. 20 is a schematic view of a section of a nasal mask manifold, describing the basic dimensional relationships. One half of a nasal interface is shown, for example, the left side or the right side. A gas delivery jet nozzle 1903 is positioned near a proximal end of the manifold and proximal to a distal end of an entrainment aperture 1907. The gas delivery jet nozzle is shown positioned in parallel with the entrainment aperture, rather than in series or coaxial. For purposes of this disclosure, parallel refers to gas flow direction. As such, the parallel position of FIG. 20 refers to the parallel flow of the ventilation gas delivered from the gas delivery jet nozzle and the flow of entrained ambient air through the entrainment aperture.

The Venturi configuration of FIG. 20 may allow the device to accomplish several important things. First, it allows the nasal interface to be as small as possible because the gas delivery jet nozzle does not obstruct the spontaneous breathing path. If the gas delivery jet nozzle is in the spontaneous breathing path, the area around the gas delivery jet nozzle likely must be bigger to compensate for the space taken up by the gas delivery jet nozzle so that the flow path is not made too resistive. Additionally, the parallel entrainment aperture may allow the device to channel the gas flow away from the mouth. Also, locating the entrainment aperture parallel to the gas delivery jet nozzle may reduce the sound created by the gas delivery jet nozzle. An outer tube can be a nasal cushion or a manifold. The outer tube in the schematic is shown expanding from a proximal end to a distal end, but it could have a constant cross section. Additionally, the outer tube may be straight or curved. The area included inside the gas delivery path being emitted from the nozzle, depicted by cone, that is, inside and to the left of the cone, may have positive pressure, and the area to the right of and outside of the cone may have negative pressure.

Dimension "A" is distance from a tip of the gas delivery jet nozzle to a distal end of the entrainment aperture. Dimension "B" is a length of throat area of device. "A"+"B" should be kept to a minimum length while still (1) producing the entrainment desired, (2) producing the positive pressure desired, and (3) minimizing the overall size for user acceptance. Optimizing size, sound and output pressure and flow require an ideal dimension for "A"+"B". Moving the gas delivery jet nozzle to the distal end of the entrainment aperture, may set dimension "A" negative, which may require a commensurate increase in "B" which is undesirable. Increasing "A" may move the gas delivery jet nozzle distally, and cause an increase in noise, which is undesirable. Positioning the tip of the gas delivery jet nozzle in the middle of the entrainment aperture may optimize pressure and flow performance while minimizing size and noise. An angled gas delivery jet nozzle may further reduce sound generation. One or more gas sampling ports may be located in the nasal interface, such as for $ETCO_2$ or $FIO_2$ sampling.

The dimensions of key functional features may be selected and varied to optimize the primary critical performance attributes such as sound, entrained flow, and output pressure. Functional features may include, but are not limited to: throat length and diameter, input pressure to the gas delivery nozzle, input flow rate to the gas delivery nozzle, nozzle exit diameter, nozzle end internal diameter radius, gas exit velocity from the gas delivery nozzle, breathing resistance of the mask, entrainment aperture size, gas delivery jet nozzle distance to the entrainment aperture, gas delivery nozzle distance to the throat entrance, exhaust flow path cross sectional area, gas delivery nozzle, and gas delivery nozzle concentricity.

Because the dimensions of functional features may compete with one another in a way that can oppositely affect performance attributes, these variables preferably must be balanced to create a successful device. If throat diameter is decreased, pressure and flow can increase, however, breathing resistance may increase, which is undesirable. If the gas delivery jet nozzle is moved further away from the throat, pressure and entrainment may increase, however, noise may also increase, which is undesirable. If the entrainment aperture cross sectional area is increased, entrainment can increase, however, a bigger overall device may be needed to accommodate the larger entrainment aperture. The entrainment aperture is dimensioned such that it is about 0-50% and preferably 10-20% more than the minimum cross sectional area of the throat section to ensure that the entrainment aperture does not restrict breathing resistance, and to optimize entrainment while limiting the overall size of the device. If the entrainment aperture location is at the proximal end of the device, approximately a 2-5× entrainment factor can be achieved (3 to 5 times more entrained flow than delivered flow). If the entrainment aperture is on a side of the device, approximately a 1-3× entrainment factor can be achieved. The side configuration may be selected to optimize the balance between output and the intended application in which it is desired to direct exhaled flow in a natural direction away from the face. If the gas delivery jet nozzle diameter is reduced, the exit velocity can increase and the entrainment can increase, however, this can reduce the output pressure, so a balance is selected. The overall length is selected so that fully developed positive pressure flow is achieved before the flow path turns to the nasal cushions section of the nasal interface, for optimal flow and pressure performance.

Embodiments of the present invention may achieve up to 35 $cmH_2O$ lung pressure (output pressure) and up to 150 lpm total flow (delivered flow plus entrained flow), and a sound level of 30-60 dB.

Figure 22B:
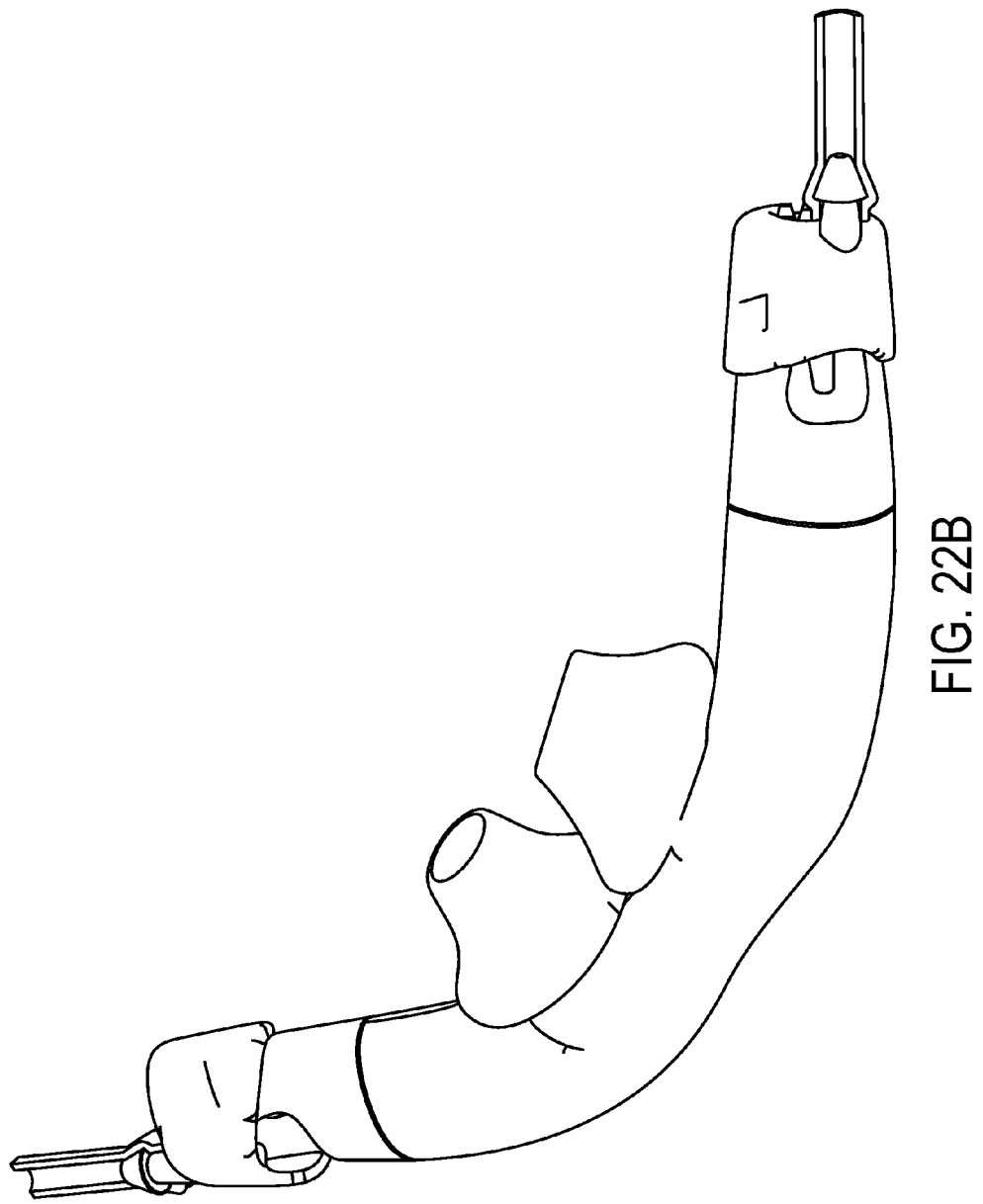
Figure 22D:
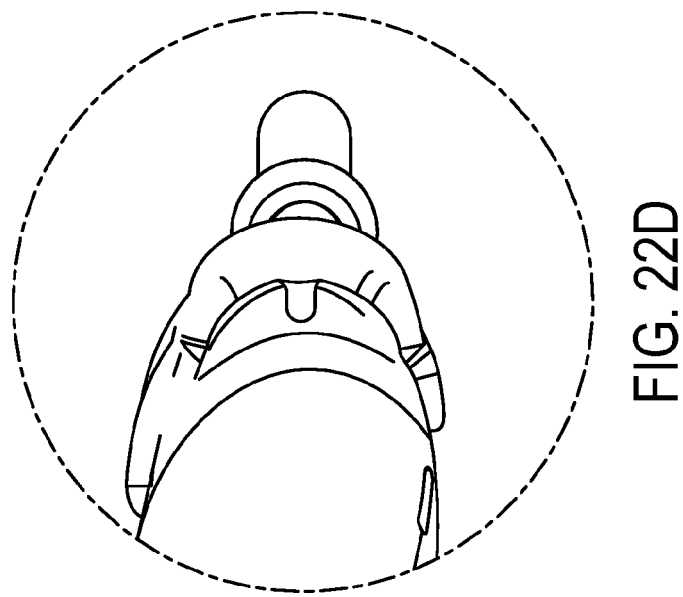
Figure 22C:
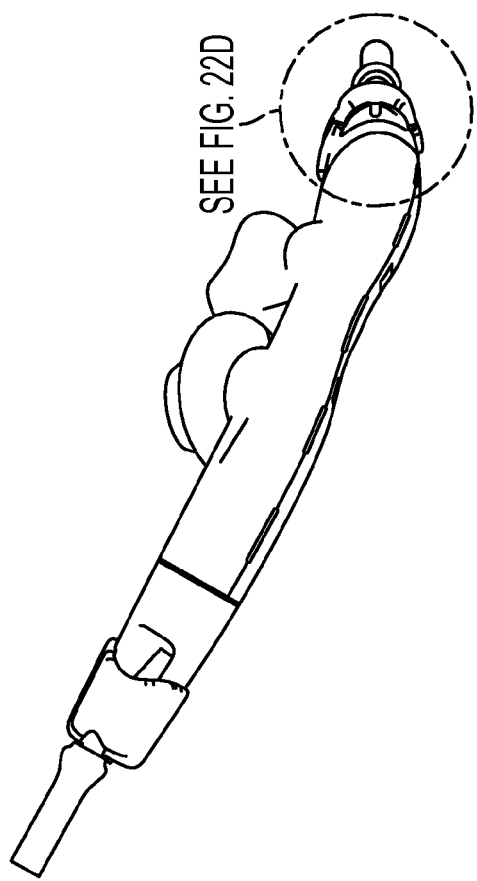

FIG. 22A shows an alternate exemplary embodiment of a nasal mask with attachments 2101 at entrainment ports 1505. Attachments 2101 may provide, for example, sampling of expired gases from a patient. This may be beneficial for harvesting of patient gases for processing, such harvesting of $CO_2$ for $CO_2$ sensing or for analyzing other possible chemicals as chemical fingerprints that are associated with different disease states or conditions. Additionally or alternatively, the attachments 2101 may allow for applying additional gas, such as therapeutic gas, oxygen or others, for patients. For example, additional oxygen may be beneficial for patients requiring highly elevated FiO2 (fractional inspired oxygen) levels. FIG. 22B shows a perspective view of the exemplary embodiment of FIG. 22A. FIG. 22C shows an alternate perspective view of the exemplary embodiment of FIG. 22A, and FIG. 22D shows a detail of the attachment 2101 of FIG. 22C. The attachments 2101 may snap or otherwise be attached either permanently or temporarily to the manifold 505 and/or gas delivery circuit connection 614 617. The attachment 2101 may cover a portion of the entrainment port 1505, but preferably does not affect the size of the entrainment port 1505. Preferably, the attachment 2101 does not add a significant amount of resistance to the gas flow path. An opening/barb fitting 2103 may allow coupling of a tube or sensing lumen (not shown). The attachment 2101 may create a pocket or space between the attachment 2101 and the manifold 505 and/or gas delivery circuit connection 617. The pocket or space may allow for addition or removal of gas to the main gas pathway.

Figure 23A:
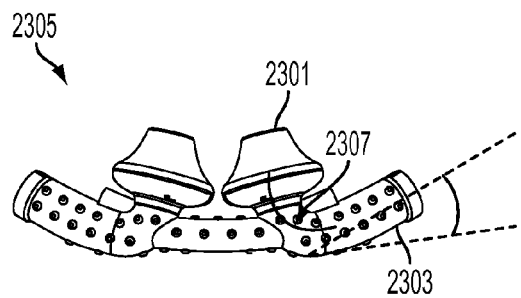
FIGS. 23A-23D show exemplary embodiments of the nasal mask with various dimensions.
Figure 23B:
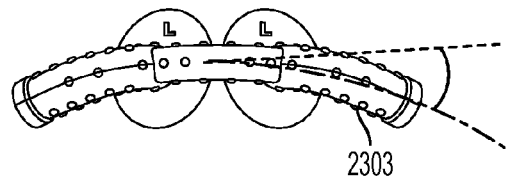
Figure 23C:
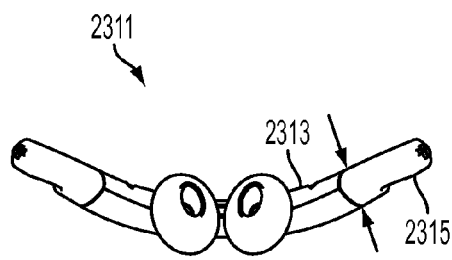
Figure 23D:
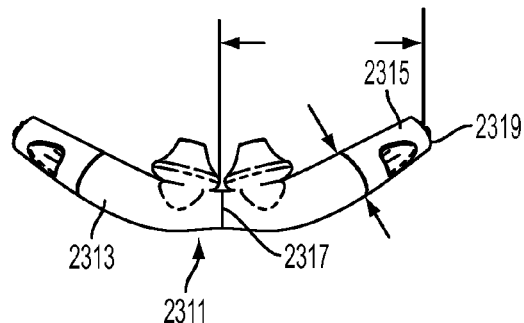

FIGS. 23A-23D show exemplary embodiments with various dimensions. FIG. 23A shows a front view of a compliant tube 2305. A radius of curvature 2307 from a substantially vertical segment of the nasal pillows 2301 to an arm 2303 of the compliant tube 2305 may be approximately 0.1 to approximately 0.5 inches, more preferably approximately 0.2 to approximately 0.4 inches, and more preferably approximately 0.25 inches. An angle between the centerline of the arm 2303 and horizontal may be approximately 15 to approximately 45 degrees, more preferably approximately 20 to approximately 40 degrees, and more preferably about 30 degrees. FIG. 238 shows a bottom view of the compliant tube 2305. An angle between the centerline of the arm 2303 and the centerline of the central section of the compliant tube 2305 may be approximately 10 to approximately 40 degrees, more preferably, approximately 15 to approximately 35 degrees, and more preferably about 25 degrees. FIG. 23C shows a back perspective view of the device 2311. A diameter along the connection between the manifold 2313 and the gas delivery connector 2315 may be approximately 0.1 to approximately 1.0 inches, more preferably approximately 0.2 to approximately 0.8 inches, and more preferably approximately 0.45 inches. FIG. 23D shows a front view of the device 2311. A diameter along the connection between the manifold 2313 and the gas delivery connector 2315 may be approximately 0.2 to approximately 1.0 inches, more preferably approximately 0.3 to approximately 0.8 inches, and more preferably approximately 0.55 inches. A distance from a centerline 2317 to a proximal end 2319 may be approximately 1 to approximately 3 inches, more preferably approximately 1.2 to approximately 2.8 inches, and more preferably approximately 2.25 inches.

Figure 24:
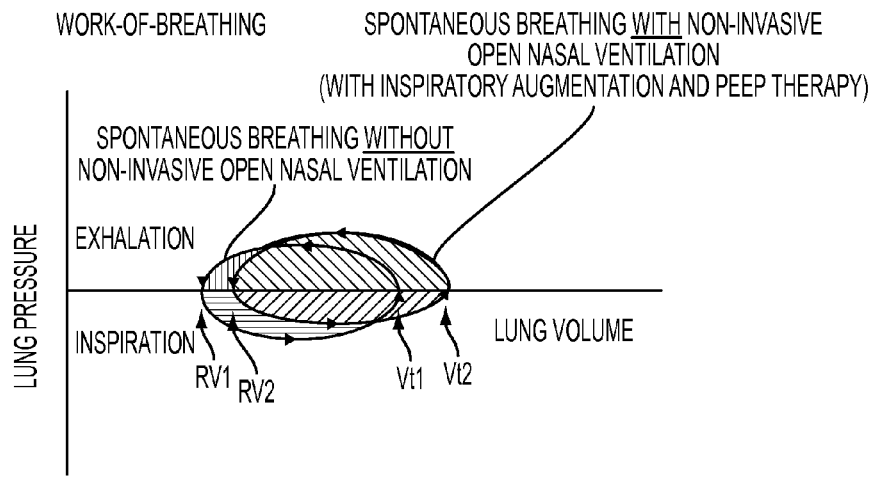
FIG. 24 graphically shows how the patient's work of breathing may be beneficially affected by the invention when the invention is used for lung disease or neuromuscular disease applications.

FIG. 24 describes the mechanism of action of the invention, and how the patient's work of breathing may be beneficially affected by the invention, when the invention is used for lung disease or neuromuscular disease applications. The patient's lung volume may be graphed as a function of lung pressure, the area inside the curve representing work, typically expressed in Joules per Liter (J/L), and for a normal healthy adult can be 0.3-0.6 J/L. For a respiratory compromised patient, 4-10 times more work can be required to breathe during rest, and even more during exertion, to overcome the diseased state of the tissue, for example to overcome static and dynamic hyperinflation as in the case of COPD, or to overcome high airways resistance as in the case of fibrosis or ARDS.

In the graph shown, the area inside the curve below the pressure axis is the inspiratory WOB, and the area defined by the area inside the curve above the pressure axis is the expiratory WOB. The arrows show the progression of a single breath over time, starting from RV to VT then returning from VT to RV. RV1 and VT1 are the residual volume and tidal volume without the therapy. Line represents spontaneous breathing without non-invasive open nasal ventilation. Line represents spontaneous breathing with non-invasive open nasal ventilation, with inspiratory augmentation and positive end-expiratory pressure (PEEP) therapy. RV2 and VT2 are the residual volume and tidal volume with the therapy. As can be seen, RV increases with the therapy because in this example, expiratory flow is provided as part of the therapy, which may increase residual volume. Importantly, VT is increased with the therapy and is increased more that the RV is increased, indicating that more volume is entering and leaving the lung as a result of the therapy. The increase in tidal volume is considered clinically efficacious, however is technically challenging to achieve in an open ventilation, non-invasive and minimally obtrusive system. As is shown in the graph, the patient's inspiratory WOB with the invention ON may be about 25% less than the patient's inspiratory WOB with the invention OFF. Also, inspiratory lung pressure increases (is less negative) and tidal volume increases, and optionally exhaled pressure increases if the therapy is provided during exhalation. While residual volume increases in the example shown because the ventilator is providing gas in this example during the expiratory phase, the ventilation parameters can be titrated to not effect residual volume, and because of the ability of the patient to exercise their lung muscles when receiving the therapy, the patient's lung mechanics may remodel in the case of COPD, actually causing a reduction of residual volume to a more normal value. In the graph shown, the waveform with therapy assumes an early inspiratory trigger time for the ventilator inspiratory phase therapy output, and that the volume output is delivered within the patient's inspiratory time. Optionally, however, different delivery waveforms and delivery synchronizations can be performed, which may adjust the WOB curve. For example, the ventilator inspiratory phase therapy can be delivered late in the person's inspiratory cycle, with delivery completing at the end of inspiration, and delivered with a square or ascending waveform profile. In this case the WOB curve with therapy will be tilted upward to the right of the curve, such that inspiration ends and transitions to exhalation at a point above the lung pressure zero axis.

Figure 25:
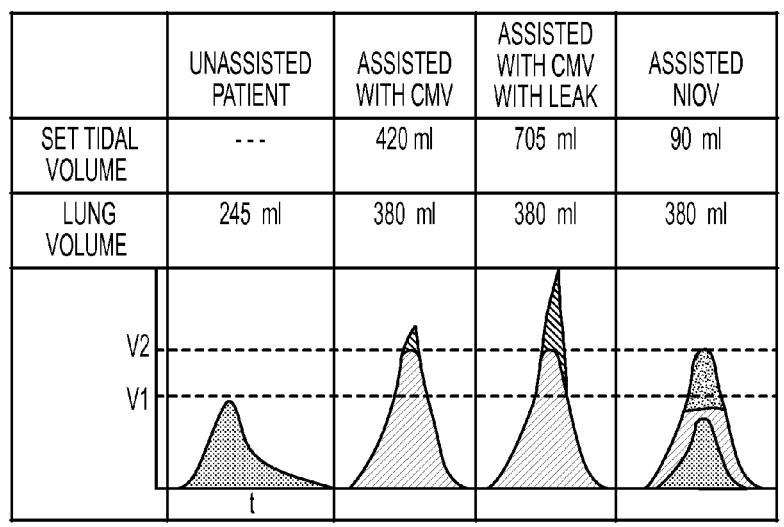
FIG. 25 graphically shows lung volume on the x-axis and lung pressure on the y-axis to illustrate how the lung volumes achieved with NIOV on a lung simulator bench model in comparison to conventional ventilation.

FIG. 25 graphically illustrates the lung volumes achieved with NIOV on a lung simulator bench model in comparison to conventional ventilation. In all the waveforms the simulated patient is spontaneously breathing at the same inspiratory effort which results in a tidal volume of 245 ml, and the clinical goal is to increase the patient's tidal volume from 245 ml to 380 ml. In the first waveform from left to right in the graph, the patient's breath is un-assisted and thus the patient receives a tidal volume of 245 ml. In the next waveform, the simulated patient with the same effort is assisted with a traditional closed system ventilator, such as with a sealed breathing mask or cuffed airway tube. The ventilator output is set to a level to achieve the desired "assisted" tidal volume of 380 ml. The ventilator is set to 420 ml to achieve this goal, as there is a discrepancy between the gas delivered to the lung by the ventilator versus the gas delivered by the ventilator but not reaching the lung and wasting to ambient. In the third waveform, a small leak is introduced in the conventional ventilator system, such as would be done in the case of weaning the patient off of the ventilator. To achieve the desired "assisted" tidal volume of 380 ml, the ventilator must now be set at 705 ml. In the second and third waveforms, it can also be seen that all of the volume received by the patient's lung originates from the ventilator, which it must in these conventional systems. In the forth waveform, the patient is assisted with the NIOV, and as can be seen, the NIOV ventilator output only has to be set at 90 ml to achieve desired "assisted" level of 380 ml. In this case, only some of the 380 ml tidal volume comes from the ventilator, and a substantial portion of the 380 ml comes from entrainment and spontaneously inspired ambient air, therefore making the NIOV system far more efficient, comfortable, and healthier, than the other systems.

The lung pressure resulting from the therapy may be governed by a combination of factors: the gas delivery circuit pressure, the jet pump design and configuration, the patient's lung compliance and airway resistance, the patient's breathing effort, the timing of the ventilator output relative to the patient's inspiratory phase, and the ventilator output waveform. Typically, however, a gas delivery circuit pressure of 30 psi delivering 100 ml with a square waveform, and delivered for 500 msec starting at the beginning of the patient's inspiratory phase, may increase lung pressure by 5-15 cmH$_2$O. And, typically a gas delivery circuit pressure of 30 psi delivering 250 ml with a trapezoidal waveform, and delivered for 700 msec during the majority of the patient's inspiratory phase, may increase lung pressure by 10-25 cmH$_2$O. The gas delivered by the ventilator can be oxygen, air, oxygen-air mixtures, or therapeutic gases such as helium. In a main mechanism of action of the invention, the patient's lung pressure and lung volume is increased, which allows the patient to exert themself without being limited by fatigue and dyspnea. In another main mechanism of action of the invention, the patient reduces their breathing effort in response to the pressure and volume support provided by the therapy, thus resulting in no change in total lung volume from the therapy, but resulting in a reduced work of breathing. In another main embodiment of the invention, a combination of the above two mechanisms of action can occur.

Figure 26:
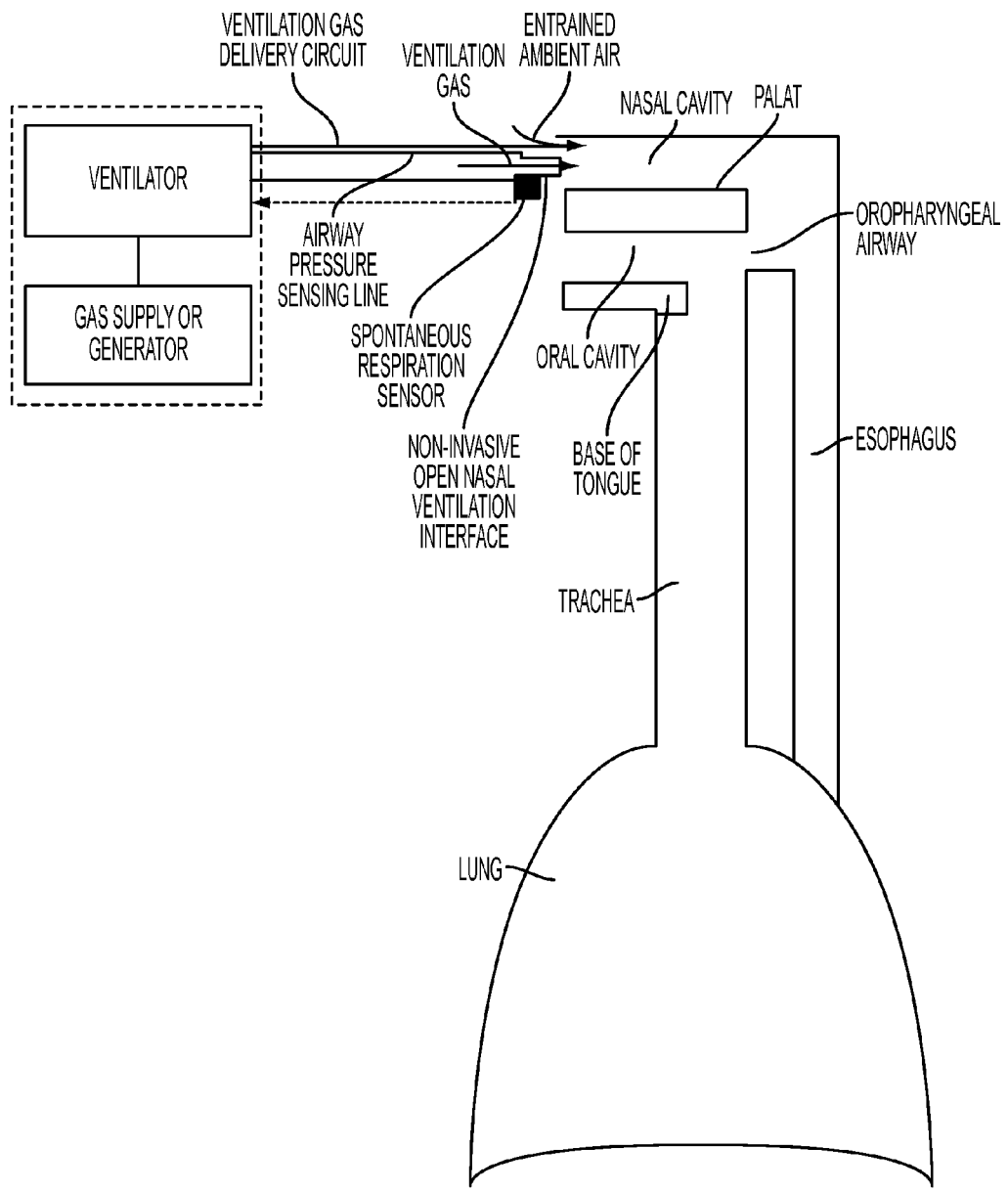
FIG. 26 describes a system schematic diagram when the invention is used for treating sleep apnea.

FIG. 26 describes a schematic diagram of an exemplary overall system when used to treat sleep apnea. In this embodiment, a ventilator delivers gas to a nasal interface from a gas generating system, such as a scroll pump.

The nasal interface geometry and dimensions may optimize the physics and fluid dynamics of the system to maximize performance, and user acceptable and tolerability. The performance of the system may create an increase in lung volume, or increase in lung pressure, or reduction in the work-of-breathing of the user, or increase in airway pressure.

Ventilation gas can be oxygen as in the case of respiratory insufficiency applications, air in the case of sleep apnea or neuromuscular applications, combinations thereof, or any other clinically beneficial gas.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

What is claimed is:

1. A system for providing ventilation to an individual, the system comprising:
   a rigid or semi-rigid manifold housing;
   a compliant tube within the manifold housing for forming a main gas pathway through the manifold housing;
   a gas delivery circuit fluidly coupled to the main gas pathway, wherein the gas delivery circuit includes:
      at least one gas delivery circuit connection being coupleable to the manifold housing; and
      a sensing extension tube associated with the at least one gas delivery circuit connection and extending from a distal end thereof;
   at least one entrainment port defined through a wall of the at least one gas delivery circuit connection in fluid communication with ambient air; and
   one or more nasal connectors fluidly coupled to the main gas pathway in the compliant tube.

2. The system of claim 1, wherein the manifold housing is a multi-piece manifold housing.

3. The system of claim 1, wherein the main gas pathway of the compliant tube is devoid of corners and abrupt bends and angles.

4. The system of claim 1, wherein the compliant tube is substantially straight in a relaxed state.

5. The system of claim 1, wherein the manifold housing has compound arcuate curves.

6. The system of claim 5, wherein the compound arcuate curves curve laterally from a midline, posteriorly and superiorly.

7. The system of claim 1, wherein the compliant tube further comprises one or more bumps to create space between the compliant tube and an inner surface of the manifold housing.

8. The system of claim 1, wherein the one or more nasal connectors each have an offset distal end relative to a base of each of the one or more nasal connectors.

9. The system of claim 1, wherein the one or more nasal connectors are coupled to the manifold housing.

10. The system of claim 1, wherein the one or more nasal connectors are coupled to the compliant tube within the manifold housing.

11. The system of claim 10, wherein a gimbaling zone of each of the one or more nasal connectors extends below an outer surface of the manifold housing.

12. The system of claim 1, wherein the compliant tube and the one or more nasal connectors are continuous.

13. The system of claim 1, wherein the one or more nasal connectors are one or more nasal pillows.

14. The system of claim 1, further comprising an inner tube retaining ring for coupling the compliant tube to the manifold housing at opposite proximal ends of the compliant tube.

15. The system of claim 1, wherein the main gas pathway is divided into a left gas pathway and a right gas pathway, and further comprising an interconnecting channel between the left as pathway and the right gas pathway.

16. The system of claim 1, further comprising one or more sensing ports.

17. The system of claim 16, wherein the one or more sensing ports are located on a stem of at least one of the one or more nasal connectors.

18. The system of claim 16, further comprising a sensing tube guideway within the manifold housing for receiving at least a portion of the sensing extension tube.

19. The system of claim 18, wherein the sensing tube guideway is located to align a distal end of the sensing extension tube with a proximal opening of one of the one or more sensing ports.

20. The system of claim 16, wherein the one or more sensing ports are one or more sensing ports for each nostril.

21. The system of claim 1, further comprising one or more nozzles within the manifold housing for delivering ventilation gas to the individual.

22. The system of claim 1, wherein the at least one entrainment ports are at least one entrainment port on each of one or more proximal ends of the manifold housing.

23. The system of claim 1, wherein the manifold housing further comprises an attachment near the at least one entrainment port for harvesting patient expired gases.

24. The system of claim 1, wherein the manifold housing further comprises an attachment near the at least one entrainment port for introducing additional gas.

25. The system of claim 24, wherein the additional gas is oxygen.

26. The system of claim 1, wherein the at least one gas delivery circuit connection is configured to be removeably connected to the proximal end of the manifold housing.

27. The system of claim 1, further comprising at least one jet nozzle within the manifold housing for delivering ventilation gas to the individual, wherein the at least one entrainment port is in downstream proximity to the at least one jet nozzle.

28. The system of claim 27, wherein a combination of ventilation gas delivered from the at least one jet nozzle and a flow of entrained ambient air through the at least one entrainment port provide ventilatory support.

29. A system for sensing airflow through a patient's nose, the system comprising:
   a manifold;
   a sensing port with a distal opening that opens to a main gas pathway, the main gas pathway being formed by a compliant tube within the manifold;
   a protrusion on at least one side of the distal opening that protrudes into the main gas pathway;
   a gas delivery circuit fluidly coupled to the main gas pathway, wherein the gas delivery circuit includes:
      at least one gas delivery circuit connection being coupleable to the manifold; and
      a sensing extension tube associated with the at least one gas delivery circuit connection and extending from a distal end thereof; and
   at least one entrainment port defined through a wall of the at least one gas delivery circuit connection in fluid communication with ambient air.

30. The system of claim 29, wherein the distal opening is located proximal to nose.

31. The system of claim 30, further comprising one or more nasal connectors fluidly coupled to the main gas pathway in the compliant tube, wherein the distal opening is located near a stem of at least one of the one or more nasal connectors or a base of at least one of the one or more nasal connectors.

32. The system of claim 29, wherein the distal opening is in the compliant tube.

33. The system of claim 29, wherein the protrusion is located on a proximal side of the sensing port.

34. The system of claim 29, wherein the protrusion extends approximately 0.01 to approximately 0.2 inches into the main gas pathway.

35. The system of claim 29, wherein the sensing port is located within the manifold.

36. The system of claim 35, wherein the manifold is a nasal interface.

37. The system of claim 35, wherein the manifold is a CPAP mask.

* * * * *